US012558559B2

(12) United States Patent (10) Patent No.: US 12,558,559 B2
Laubscher (45) Date of Patent: Feb. 24, 2026

(54) THERAPEUTIC DEVICE FOR CELL THERAPY OR CELL STIMULATION

(71) Applicant: ActivCell Group AG, Mosen (CH)

(72) Inventor: Urs Laubscher, Liestal (CH)

(73) Assignee: ActivCell Group AG, Mosen (CH)

( * ) Notice: Subject to any disclaimer, the term of this patent is extended or adjusted under 35 U.S.C. 154(b) by 872 days.

(21) Appl. No.: 17/784,000

(22) PCT Filed: Dec. 10, 2020

(86) PCT No.: PCT/EP2020/085655
§ 371 (c)(1),
(2) Date: Jun. 9, 2022

(87) PCT Pub. No.: WO2021/116358
PCT Pub. Date: Jun. 17, 2021

(65) Prior Publication Data
US 2023/0012949 A1 Jan. 19, 2023

(30) Foreign Application Priority Data

Dec. 10, 2019 (EP) .................................... 19214663

(51) Int. Cl.
*A61N 1/44* (2006.01)
(52) U.S. Cl.
CPC .................................... *A61N 1/44* (2013.01)
(58) Field of Classification Search
CPC .......... A61N 1/44; A61N 1/0468; A61N 1/06;
A61N 1/36034; A61N 1/40; A61B
2018/0091; A61B 2018/1405; A61B
18/042; H05H 1/24; H05H 1/245; H05H
2245/30; H05H 2245/34

USPC .......................................................... 606/41
See application file for complete search history.

(56) References Cited

U.S. PATENT DOCUMENTS

| 4,226,246 A | 10/1980 | Fragnet |
|---|---|---|
| 5,866,082 A | 2/1999 | Hatton et al. |
| 8,103,340 B2 | 1/2012 | Viöl |
| 2004/0267333 A1 | 12/2004 | Kronberg |
| 2011/0022043 A1 | 1/2011 | Wandke et al. |
| 2012/0107896 A1 | 5/2012 | Wandke et al. |

(Continued)

FOREIGN PATENT DOCUMENTS

| DE | 2822892 A1 | 11/1978 |
|---|---|---|
| DE | 10324926 B3 | 2/2005 |

(Continued)

OTHER PUBLICATIONS

International Search Report issued for PCT/EP2020/085655 on Feb. 4, 2021, 9 pages.

(Continued)

*Primary Examiner* — Beverly M Flanagan
(74) *Attorney, Agent, or Firm* — Hard IP Professional Services LLC

(57) ABSTRACT

A therapeutic device for cell stimulation or cell therapy comprises a housing which contains an electrode, a generator for generating high-frequency pulses, a processor unit comprising a control, regulation and calculation module, a memory unit, a control element, a controllable modulator, by means of which the generator can be controlled. A voltage pulse sequence comprising a plurality of voltage pulses can be generated by means of the modulator, wherein the frequency of the voltage pulse sequence can be at least partially not constant.

19 Claims, 24 Drawing Sheets

(56) References Cited

U.S. PATENT DOCUMENTS

| 2014/0214118 | A1 | 7/2014 | Greiner et al. |
| 2014/0219894 | A1 | 8/2014 | Ikegami et al. |
| 2019/0117969 | A1 | 4/2019 | Schmidt et al. |

FOREIGN PATENT DOCUMENTS

| DE | 102008045830 | A1 | 3/2010 |
| EP | 2163143 | B1 | 3/2010 |
| EP | 2397187 | A1 | 12/2011 |

OTHER PUBLICATIONS

Written Opinion issued for PCT/EP2020/085655 on Feb. 4, 2021, 6 pages.

Fig. 4a (PRIOR ART)
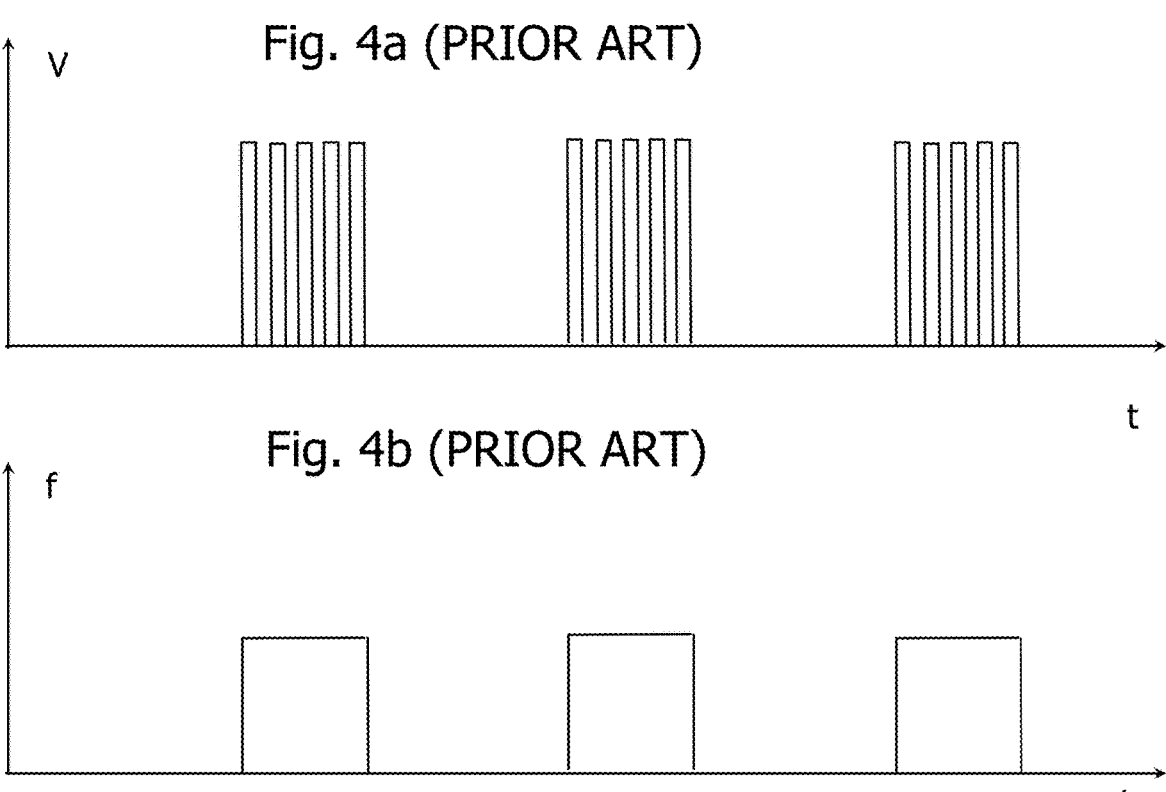
Fig. 4b (PRIOR ART)
Fig. 5a
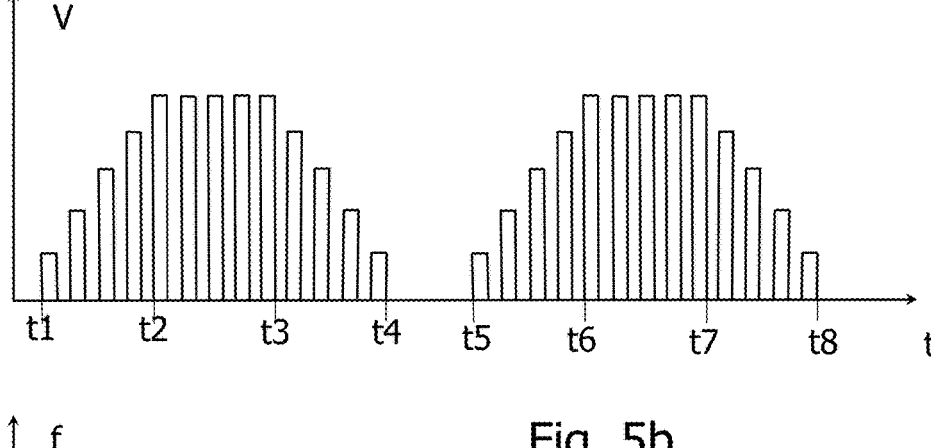
Fig. 5b
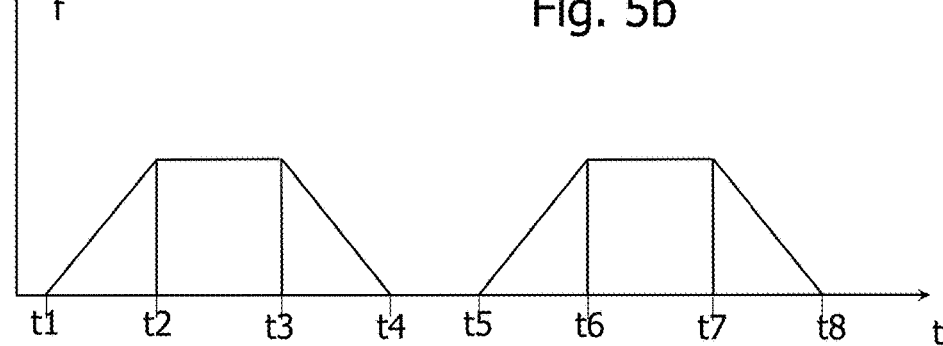

71   A   17   72
A
12

L1   L2
21   1   23   25   24   22

85   B 83   84
B
81   18   82

L1   L3
21   1   23   25   24   22

L1   L4
21   1   23   25   24   22

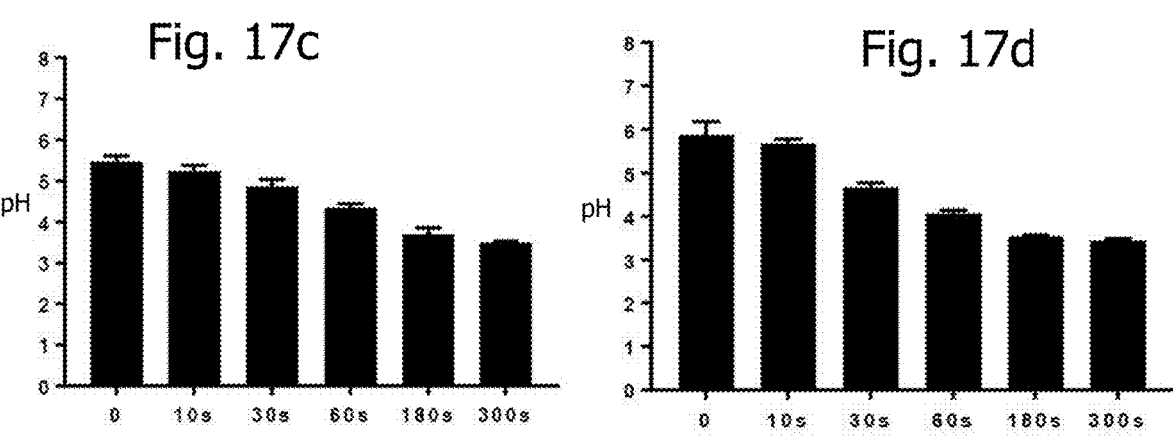
Fig. 17c
Fig. 17d
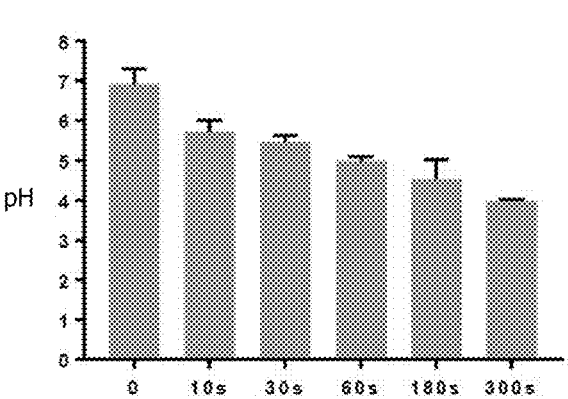
Fig. 17e
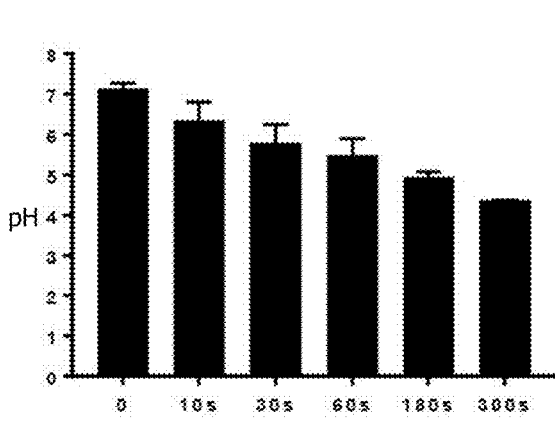
Fig. 17f
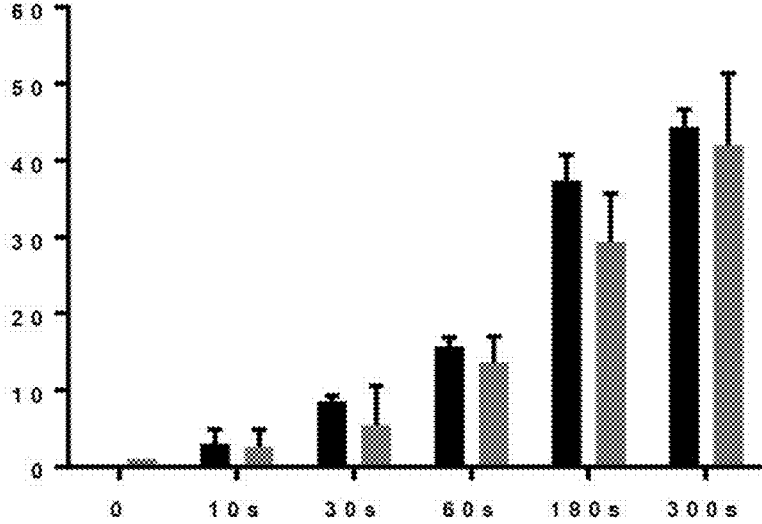
Fig. 18a Fig. 23
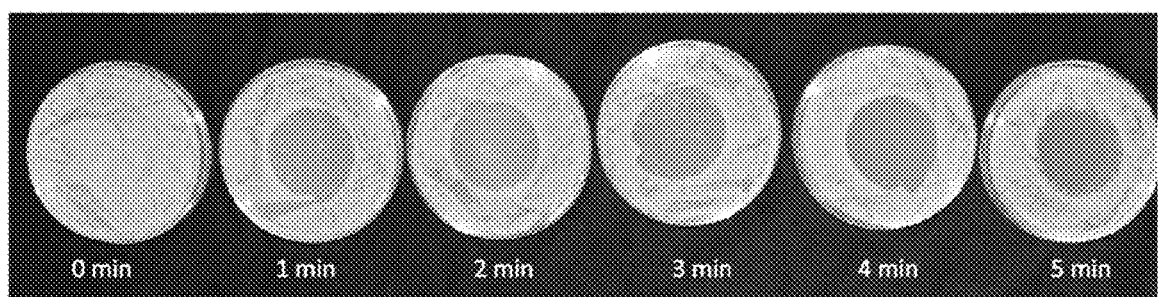
Fig. 24
Fig. 25
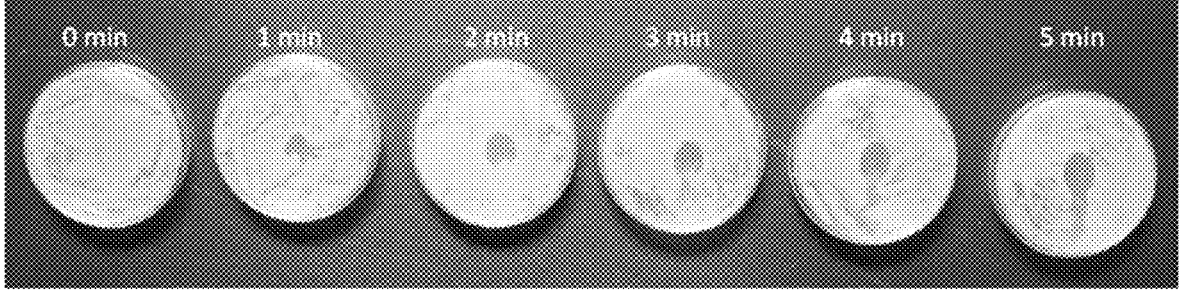

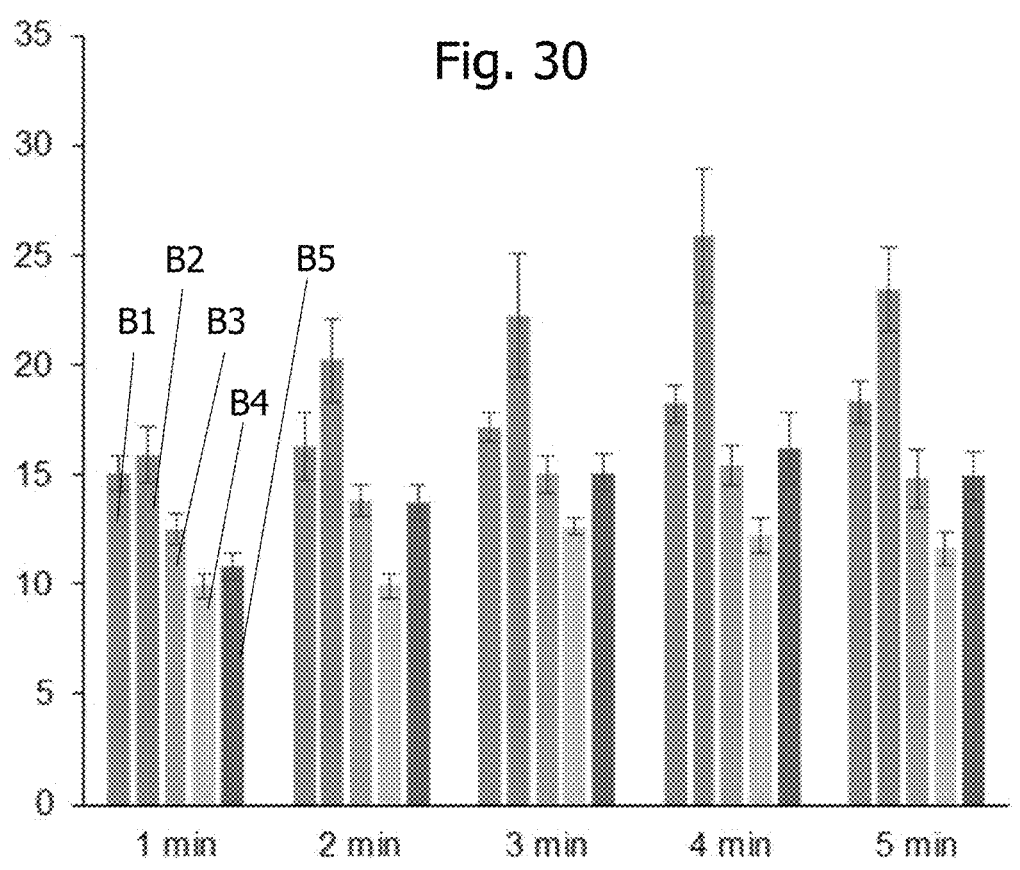
Fig. 30
Fig. 31
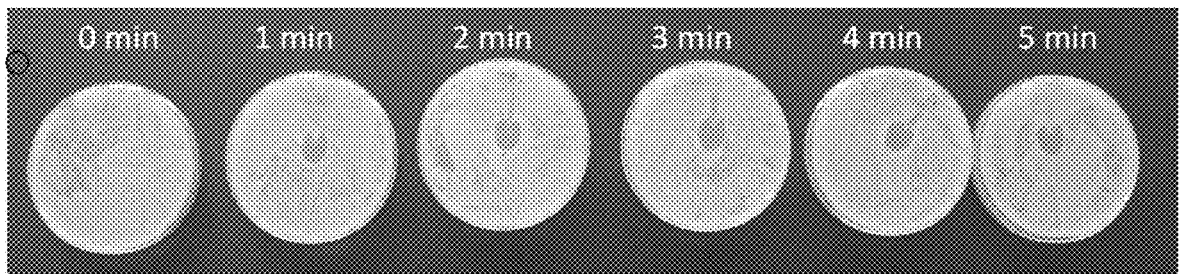
Fig. 32
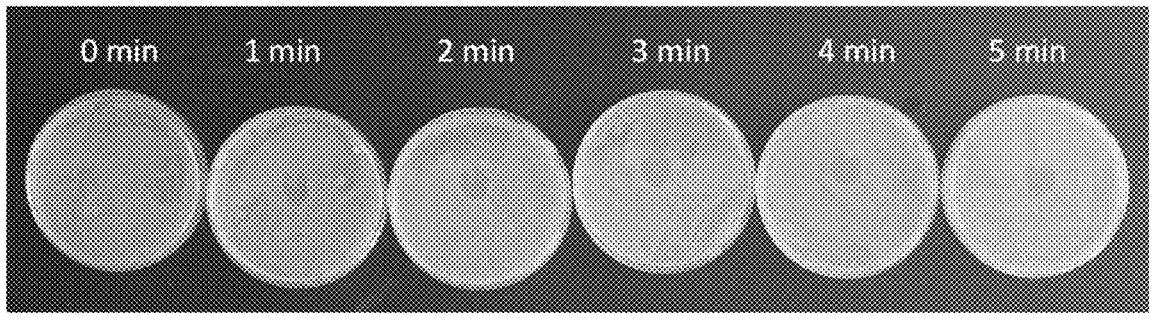

THERAPEUTIC DEVICE FOR CELL THERAPY OR CELL STIMULATION

CROSS REFERENCE TO RELATED APPLICATIONS

This application is a U.S. national stage filing under 35 U.S.C. 371 of international patent application no. PCT/EP2020/085655, filed on Dec. 11, 2020, which claims priority to European patent application no. EP19214663.7, filed on Dec. 10, 2019, the contents of both of which are incorporated herein by reference in their entirety.

TECHNICAL FIELD

The present invention relates to a therapeutic device for cell therapy or cell stimulation.

DESCRIPTION OF RELATED ART

Therapeutic devices are known from the prior art which use the technology of physiological electrostimulation, also referred to as electrotherapy in the literature. Therapeutic devices of this type are based on the principle of delivering electrical energy to the biological cell. This technology is used in medicine for so-called high-frequency therapy. An electric field generated by an RF generator is combined with a delivery device for delivering the RF power in pulses to the cell to enable cell stimulation.

The field of application of the therapeutic device according to the invention lies in the area of wellness applications, fitness, cosmetics, pain reduction, wound healing, for cell therapy or further cell stimulation for treatment in humans or animals.

Document DE 2822892 A1 shows an example of such a therapeutic device, namely a device for maintaining the negative potential of human, animal, and plant cells and/or for penetrating substances into the cells. A generator that can be influenced by means of a control circuit generates high-frequency pulses with an adjustable repetition frequency and duration, and an electric circuit generates a DC voltage and a pulsating DC voltage for ionization and pulses of a specific shape and variable repetition frequency for faradization of the tissue to be treated. A therapy session is conducted over a predetermined time interval.

Although acceptable results are achieved with this previously known therapeutic device with regard to its intended use, the following disadvantages occur for the user during operation:

The device is cumbersome to use during the therapy because a wired power supply is required, the energy level is set via a manual control on the power supply unit, the pulse frequency of the energy delivery can only be varied in a small range, namely in a range from 10 to 1000 Hz, the emitted energy cannot be influenced in its signal form.

Any of these factors limits the long-term success of the therapy, a local application of case-specific impulse forms is not possible, so that too many recurring therapy sessions have to be held and/or there is a limited effect on the cells. The treatment head containing the electrode has a diameter of approx. 17 cm and a height of approx. 10 cm. An antenna is arranged in the treatment head, which is configured as an electrically insulating plastic plate, on the surface of which a conductive covering is arranged in a circle on the patient side. A spiral conductive covering is connected at its ends to a tuning capacitor on the opposite surface.

A therapeutic device is known from EP 2397187 A1, which is fed by a direct current source. Using this therapeutic device, a magnetic field is generated to induce currents, which stimulates electrical signals in the body's nerve tracts, which can stimulate molecules, organs, or tissues of an organism. Due to the associated relatively high energy consumption, ways were sought to treat biological materials containing living cells locally with reduced energy consumption.

For example, according to DE10324926 B3, a pin-shaped electrode was provided for this purpose, which is connected to an alternating high-voltage generator. The electrode has a rounded tip covered by a dielectric. On the one hand, the dielectric serves to insulate the electrode 3, on the other hand it serves to dielectrically impede a gas discharge, which can be ignited by applying an alternating high voltage to the electrode between the dielectric and the surface of a biological material and which generates a cold plasma over the surface of the biological material. A ceramic, glass or a plasma-resistant plastic can be used as the dielectric. Free oxygen in the plasma chemically affects the biological material in order to kill undesired microorganisms, bacteria, degenerated tissue on the surface of the biological material.

DE 10 2008 045 830 A1 or EP 2 163 143 B1 discloses a device for treating an object with a plasma, the plasma being generated by means of an electrode and a counter-electrode. A dielectric is arranged between the treated object and the electrode, so that a plasma is generated by means of a dielectric barrier gas discharge, and this plasma is applied to the object to be treated. According to an embodiment, the electrode consists of an ionized gas, for example a noble gas, inert gas or gas mixture, the ionized gas being generated in that the gas is ionized by applying a high voltage that is greater than the breakdown voltage of the gas and as a plasma present. The gas thus becomes electrically conductive and can itself be used as an electrode.

Document U.S. Pat. No. 5,866,082A discloses a handheld device containing an electrode for generating a gas discharge in the air between the electrode and a body part to be treated. The electrode is configured as a glass body filled with neon, which is electrically coupled to a high-voltage transformer with a foil. The oxygen in the air between the electrode and the part of the body to be treated is stimulated to form ozone by sparking via the discharge of a capacitor located in the device. The glass body filled with neon gas prevents an electric shock in the event of damage caused by glass breakage by allowing the neon gas to escape and thereby obtaining an insulation to the transformer circuit.

Proceeding from this prior art, the object of the invention is to provide a therapeutic device which overcomes the disadvantages of the prior art. In particular, the object of the invention is to develop a therapeutic device that is easier to operate, whose pulse rate and/or energy output and/or the signal form can be individually tailored to the intended treatment or therapy by adjusting the pulse rate and/or the energy output and/or or the signal form over a wide range.

SUMMARY OF THE INVENTION

The therapeutic device for cell stimulation or cell therapy according to the invention comprises a housing which contains an electrode, a generator for generating high-frequency voltage pulses, a processor unit comprising a control, regulation and calculation module, a memory unit, at least one operating element and a controllable modulator, by means which the generator can be controlled. A voltage pulse sequence comprising a plurality of voltage pulses can be generated by means of the modulator, whereby the frequency and duration of the voltage pulses can be adjusted as desired by means of the modulator. The electrode, the generator, the processor unit, the memory unit, the operating element, and the modulator are arranged in the housing. The electrode contains a glass body containing a cavity in which a gas is located. The electrode comprises a first end couplable to the modulator. The electrode comprises a second dome-shaped end, wherein the gas can be brought into the state of a non-thermal primary plasma by the voltage pulses applied to the electrode, wherein a secondary plasma can be generated by ionization of the air which is present in the vicinity of the second end of the electrode.

The gas can in particular include an inert gas, for example helium, neon, argon. The gas is contained inside the glass body, i.e., it is enclosed in the cavity of the glass body. The gas is ionized by the introduction the voltage pulses, so that a gas discharge can take place from the electrode to the body part to be treated. The gas forms the primary plasma, which can be generated by applying the voltage, i.e., by transmitting the voltage pulse sequence. The glass body has the effect of a dielectric barrier. A secondary plasma can be obtained at the second end of the electrode by means of the primary plasma, so that the air can be ionized and thus become electrically conductive and a coupling to the body part to be treated can take place. The high voltage generated by the primary plasma is greater than the breakdown voltage, which in particular creates free oxygen or ions in the air surrounding the end of the electrode, which interact with the surface of the body part to be treated, so to induce a cell stimulation. The body part forms the cathode. In particular, if the air gap between the cathode and the first end of the glass body is less than 3 mm, a gas discharge takes place to form the secondary plasma. According to an embodiment, the electrode can contain an antimicrobial coating.

Plasma is defined as a physical state of matter in which charged particles with positive and negative charges are present in a gas phase. The sum of the positive and negative charges is the same, so that the positive and negative charges compensate each other in a volume under consideration, i.e., the overall charge state is neutral. The plasma also contains atoms or molecules with a neutral charge state, which, however, can exist in electronically, vibrationally or rotationally excited states, which are accordingly referred to as excited or reactive particles.

A non-thermal plasma is a plasma in which a temperature describing the distribution of the kinetic energy of the electrons in the plasma, referred to below as electron temperature, is higher than a temperature describing the distribution of the kinetic energy of the ions in the plasma, referred to as ion temperature subsequently. If the ion temperature is in the range of 25° C. up to and including a maximum of 100° C., the non-thermal plasma is called cold plasma.

The therapeutic device according to an embodiment of the present invention thus contains a direct atmospheric cold plasma therapeutic device. A secondary cold plasma is generated by means of the electrode containing the primary plasma. The generation of a secondary cold plasma has the advantage that there is little or no heating of the body part to be treated. The cells of the body part to be treated are therefore not exposed to any impermissible heat influence, which could lead to damage to the cells or their components.

The therapeutic device reacts to touch by changing the intensity of the plasma, so that its intensity can be changed depending on the holding position. The highest intensity was observed in the trials when the therapeutic device was held near the opposite end of the electrode. In the measurements described below, the therapeutic device was therefore wrapped in a grounded aluminum foil in order to rule out any influence on the measurement results through manual manipulation of the therapeutic device.

According to an embodiment, the generator is designed as a Tesla coil. The voltage provided by the energy storage unit is transformed to the input voltage of the generator by means of the modulator. According to an embodiment, the maximum frequency is in the range from 10 up to and including 100 Hz. According to an embodiment, the maximum voltage at the output of the modulator is in the range from 8 V up to and including 65 V. The modulator can contain a transformer, by means of which the voltage provided by the energy storage unit can be transformed to the input voltage required by the generator. According to an embodiment, the voltage at the output of the generator is in the range from 5 kV up to and including 25 kV.

According to an embodiment, the frequency or the amplitude can be adjusted using the modulator. The amplitude and/or the frequency of the voltage can be modulated by means of the modulator. According to an embodiment, the frequency of the voltage pulse sequence is at least partially not constant. According to an embodiment, the amplitude of the voltage increases during a period of time $t2-t1$, during a period of time $t3-t2$ the voltage is constant and during a period of time $t4-t3$ the voltage decreases, wherein the duration of the voltage pulse sequence corresponds to the period of time $t4-t1$.

In particular, the frequency can increase during the period $t2-t1$, the frequency can remain constant during the period $t3-t2$, and the frequency can decrease during the period $t4-t3$.

Any combination of voltages and frequencies can thus be adjusted by means of the modulator. Any desired pulse sequence can thus be adjusted by means of the modulator. The pulse sequence is transmitted to the generator and converted by the generator into a pulse sequence with a correspondingly higher voltage. The high voltage is transferred to the electrode.

According to an embodiment, an energy storage unit arranged in the housing is provided for supplying energy for operating the therapeutic device, so that the therapeutic device can be operated wirelessly. The housing can contain a display element, by means of which in particular therapy and operating data can be displayed.

According to an embodiment, the electrode comprises a sensor, by means of which the current or the voltage emitted via the electrode can be recorded as measured values, wherein the measured values are digitizable as measured data, wherein the measured data can be stored in the memory unit, wherein the calculation module of the processor unit is configured to determine the energy delivered and/or the time profile of the energy emitted by the electrode.

In particular, the control module of the processor unit is configured to control the modulator based on the measured data, in particular for controlling a constant energy output and/or for a control independent of the signal form, so that any desired signal form can be generated in the generator, for example a combination of amplitude modulation and frequency modulation. The measured data are configured to control a course of therapy by the control module of the processor unit.

According to an embodiment, the measured data in the processor unit can be linked to a time stamp, wherein the measured data linked to the time stamp are configured to be stored in the memory unit for storing the course of therapy.

According to an embodiment, the housing can be configured as one of the poles of a capacitor for a capacitive coupling.

The energy storage unit can be configured as a rechargeable element, for example as a lithium-ion element or as a supercapacitance. In particular, battery charging can be configured to operate the therapeutic device for a maximum duration of 50 minutes. The therapeutic device can be operated continuously, in particular for a period of up to 25 minutes. The operating time can be extended if the energy storage unit is cooled, or the operation of the therapeutic device is interrupted for a period of approximately 30 minutes.

According to an embodiment, the housing comprises an inner side which contains an electrically conductive or conductive surface, for example a conductive plastic or a plastic coated with an electrically conductive material. The outside of the housing is configured as an electrical insulator. In particular, the housing can contain a plastic or consist of a plastic. For example, the housing can contain ABS or consist of ABS. In particular for applications in the food sector, the housing can contain PLA (polylactide) or consist of PLA.

The therapeutic device is disposed with an improved signal output which can be configured or pre-programmed by the user depending on the type of therapy. The therapeutic device is much easier to handle due to the integrated energy storage unit, which enables wireless operation.

According to the invention, these advantages are obtainable by at least one of the following features:
   a changeable signal curve, for example a variable frequency of the high-frequency field, which is emitted via an electrode,
   the control of the intensity of the delivered energy, whereby typically the delivered power remains constant and independent of the position and/or type of the electrodes,
   an improvement of the handling by means of an energy storage unit arranged in the housing, which has its own internal power supply and is operated by means of energy cells, typically by means of a rechargeable battery.

The wireless application can be facilitated and improved by means of a new, previously unused physical principle in the therapy application. According to an embodiment, capacitive coupling is used so that the energy of the high-frequency field can flow from the user to the object to be treated. According to this embodiment, the electrode is capacitively coupled to the user and connects the user to the object to be treated by means of the electrode. The body of the user and the object to be treated ensure an equalization of a potential via the capacitive coupling.

The advantage of the invention obtainable by the controllable, programmable energy delivery including an adjustable signal form results in an optimization of various forms of therapy.

According to an exemplary form of therapy, the energy is delivered over a large surface via the variable pulse frequency of the energy delivery with simultaneous modulation of the signal form. Therewith, the concept of the skin effect is influenced, which is known to those skilled in the art. The electrons, which reach the treatment object via the high-frequency voltage emitted via the electrode, are forced predominantly to the surface of the treatment object as a result of the skin effect. The skin effect is reduced at a lower amplitude and/or frequency modulation (AM/FM), resulting in a more targeted penetration depth and duration of the energy delivery.

A modulation can be varied by the user by actuating control elements of the therapeutic device and/or by a therapeutic device configured according to the type of therapy, which reads the required modulation from a memory unit.

In a further embodiment, the energy output is measured by means of a sensor, for example by measuring a voltage and/or a current, and the measurement result is fed to the processor unit. The processor unit contains a control module, which can be used to control different states depending on the therapy method.

According to an embodiment, the energy output is modulated during the modulation in such a way that the energy output follows a signal form that can be selected independently or retrieved from the memory unit.

According to an embodiment, the energy delivery is stabilized regardless of the electrode used, the different coupling factor of the capacitive coupling through the wireless use during the therapy or the modulated signal form.

In a further variant, the measured values determined by the sensor can be made available as a signal to the processor unit, which can process the measured values as measured data. In particular, the units or measured variables mentioned below can be calculated using the calculation module. If necessary, the units can be displayed via a display element, can be output via an interface for the exchange of information, or can be stored in a memory unit.

The units can include at least one element from the list below:
   Total energy delivered in a given time interval
   Signal form and modulation type (AM/FM) during therapy
   Removal of the electrode and time interval of one or more interruptions
   Regulation of an internal energy management
   Detection of defective electrodes Further calculations are conceivable which document and register the course of therapy for each treatment object. Further calculations are also conceivable, including external data that are read in via the interface, which increase and document the success of the therapy. For this purpose, the processor unit can perform any type of calculations, typically these are controlling and/or statistical calculations.

The results of the calculations can in turn be fed into the control module of the processor unit and influence the signal curve and/or the modulation. A learning effect for a later therapy session can be generated from an earlier therapy session using therapy data. These therapy data can be communicated to other therapeutic devices via the interface for the exchange of information and thus ensure that a continuous improvement in quality is made possible by each use of the therapeutic device according to the invention.

The capacitive coupling can take place by coupling the user and the treatment object with a conductive surface on the housing of the therapeutic device. For this purpose, it is conceivable that the housing itself is designed to be electrically conductive, that is to say it has at least one electrically conductive or conductive surface, or the housing has a conductive or conductive surface on the inside. The conductive or conductive surface itself can be configured as a wire, as a surface or as a three-dimensional object.

The energy storage unit can be supplied with energy via a charging system. In a variant, this charging system includes a contact plug and can obtain the required energy from a commercially available charging station. In another possible variant, the energy storage unit is charged via an induction loop which is fitted in the housing. This induction loop forms a secondary coil of a transmission transformer. An energy flow can thus take place by means of the primary coil built into the charging station when the therapeutic device is in the effective field of the charging station. Such charging systems are now available in standardized form in the electronics industry.

BRIEF DESCRIPTION OF THE DRAWINGS

The invention is explained in more detail using an exemplary embodiment which is illustrated in the drawings. It is shown in:

FIG. 32 an illustration of the agar plates for an inhibition zone test for the EWC electrode of the second therapeutic device for the bacterium *Staphylococcus epidermidis,*

DETAILED DESCRIPTION

Figure 1A:
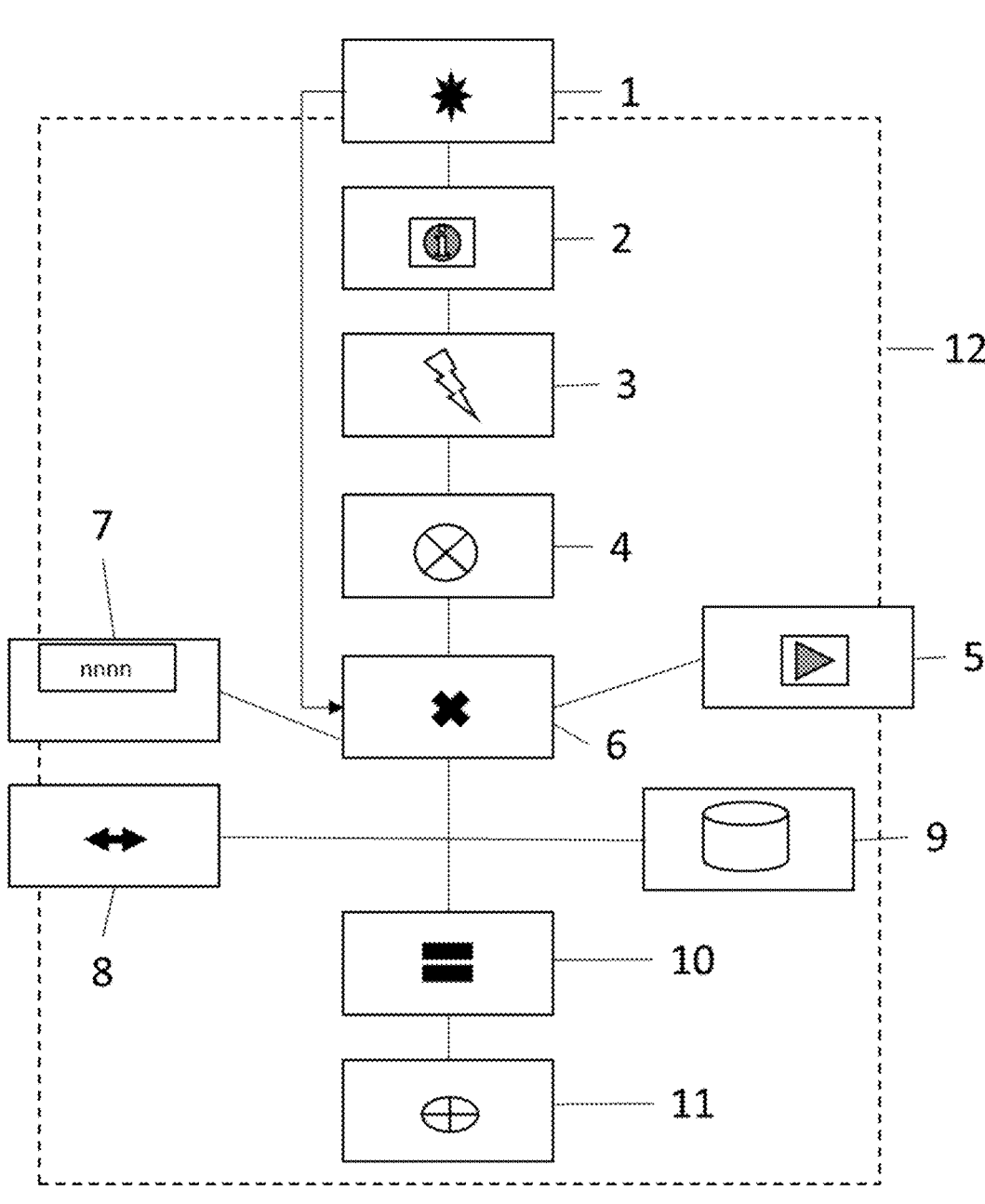
FIG. 1a: a scheme of a first embodiment of a therapeutic device.

FIG. 1*a* schematically shows a first embodiment of a therapeutic device for cell therapy, comprising an electrode 1, a generator 3 for generating high-frequency pulses, a processor unit 6 comprising a control, regulation and calculation module, a memory element 9 and operating elements 5.

The therapeutic device can include at least one interface 8 for exchanging information.

The therapeutic device also includes a memory unit 9 and a controllable modulator 4 which controls the generator 3. The energy supply for operating the therapeutic device is provided by an internal energy storage unit 10.

The housing 12 can contain at least one display element 7, by means of which, in particular, therapy and operating data can be displayed.

In addition, the therapeutic device includes a sensor 2 which measures the voltage and/or the current delivered via the electrode 1, whereby it is possible to determine the energy delivered via the electrode 1 from the measured voltage or the measured current. The current and/or the voltage delivered via the electrode 1 are thus recorded as measured values by means of the sensor.

The measured values are digitized and stored in the memory unit 9 as measured data. The energy delivered can be determined from the measured data by means of the calculation module of the processor unit 6. The temporal profile of the energy emitted by the electrode 1 can be determined by means of the calculation module of the processor unit 6 from the measured data for current and/or voltage stored in the memory unit 9 with a time stamp. Alternatively, the determined voltages and/or currents can also be recorded by a recording device and converted into measured data, so that the time profile of the energy emitted by the electrode 1 can be determined from the recorded measured data for the voltage and the current.

All components of the therapeutic device are arranged in a housing 12.

In particular, the housing 12 and/or the generator 3 can be configured in such a way that the housing or the generator form one pole of a capacitor, which enables a capacitive coupling.

According to an embodiment, the therapy, and operating data from the memory unit 9 are configured to be readable and writable. The data stored in the memory unit 9 can be used to influence the course of therapy.

According to an embodiment, the therapy and operating data can be calculated and processed in the processor unit 6 into control instructions, taking into account the measured values measured by the sensor 2, which can be stored as data in the memory unit. The control instructions can be used to control the modulator 4.

The modulator 4 can be controlled in particular in such a way that the energy output is constant and independent of the signal form.

In particular, the modulator 4 can be controlled in such a way that any desired signal form is generated in the generator 3; typically, a combination of amplitude and frequency modulation can be provided.

According to an embodiment, the housing 12 contains an electrically conductable or conductive surface, for example a conductive plastic or a plastic coated with an electrically conductable material.

According to an embodiment, the energy storage unit 10 can be configured as a rechargeable element, typically as a lithium-ion element or as a supercapacitance.

The energy delivered via the electrode 1 can be used for cell stimulation or cell therapy.

Figure 1B:
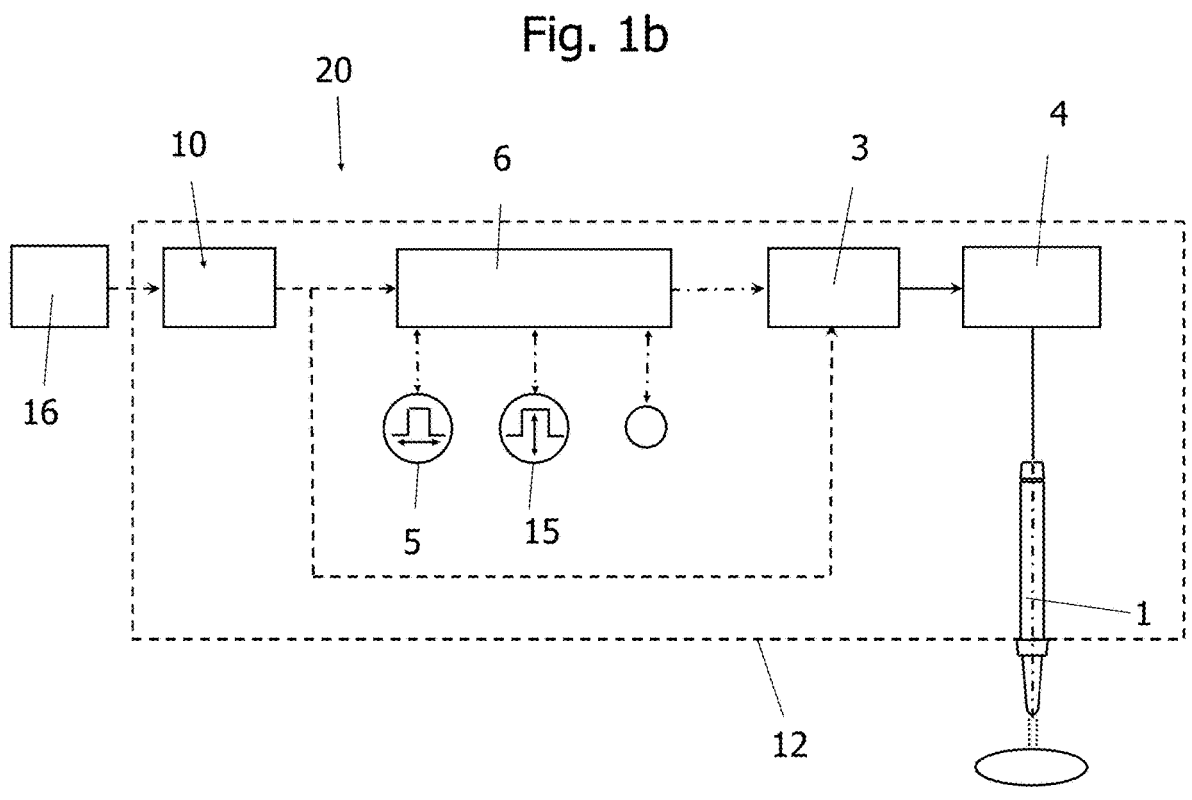
FIG. 1b: a scheme of a second embodiment of a therapeutic device.

FIG. 1*b* shows a second embodiment of a therapeutic device 20, whereby the same reference numerals as in FIG. 1*a* having been used for components which are the same or have the same effect.

The therapeutic device 20 comprises an electrode 1, a generator 3 for generating high-frequency pulses, a processor unit 6 comprising a control, regulation and calculation module and operating elements 5, 15 and an energy storage unit 10. The electrode 1, the generator 3, the processor unit 6 and the operating elements 5, 15 and the energy storage unit 10 are accommodated in the assembled state in a common housing 12, which is shown schematically as a system boundary in FIG. 1*b*.

The energy supply for operating the therapeutic device 20 takes place by means of an energy storage unit 10 which is also fitted in the housing 12. The energy storage unit 10 can in particular contain a rechargeable battery. According to an embodiment, the energy storage unit 10 can contain a lithium-ion battery or a supercapacitance. The energy storage unit 10 can be charged using a charging device 16, which is known to the person skilled in the art and is therefore not specified in more detail in this illustration.

Figure 1C:
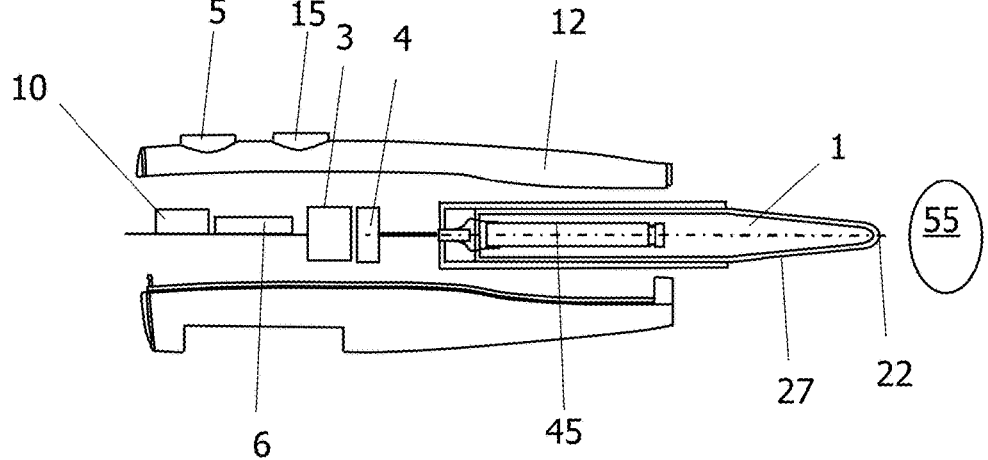
FIG. 1c: a scheme of the components of the second embodiment of the therapeutic device, FIG. 2 a simplified circuit diagram of a known therapeutic device, FIG. 3 simplified circuit diagram of the therapeutic device of FIG. 1a, FIG. 4a: a possible voltage curve over time of the known therapeutic device of FIG. 2, FIG. 4b: a possible frequency curve over time of the known therapeutic device of FIG. 2, FIG. 5a: a possible voltage curve over time of the therapeutic device of FIG. 3, FIG. 5b: a possible frequency curve over time of the therapeutic device of FIG. 3.

According to the present embodiment, the operating elements 5, 15 are rotatably arranged in the housing 12, which is visible in the schematic representation of FIG. 1*c*. The duration of each pulse can be adjusted using the operating element 5. The height of the pulse, i.e., its amplitude, can be adjusted by means of the operating element 15. According to the present embodiment, a scale is attached to each of the operating elements 5, 15, by means of which the set therapy and operating data can be displayed. In addition, the housing 12 can contain an optical display element, for example an LED light.

In addition, the therapeutic device includes a sensor 2 which measures the voltage and/or the current delivered via the electrode 1, wherein the energy delivered via the electrode 1 can be determined from the measured voltage or the measured current. The current and/or the voltage delivered via the electrode 1 are thus recorded as measured values by means of the sensor. The measured values are digitized and stored in the memory unit 9 as measured data. The energy delivered can be determined from the measured data by means of the calculation module of the processor unit 6. The time profile of the energy emitted by the electrode 1 can be determined from the measured data for current and/or voltage stored in the storage unit 9 with a time stamp by means of the calculation module of the processor unit 6. Alternatively, the determined voltages and/or currents can also be recorded by a recording device and converted into measured data, so that the time profile of the energy emitted by the electrode 1 can be determined from the recorded measured data for the voltage and the current.

According to an embodiment, the therapy and operating data can be calculated and processed in the processor unit 6 into control instructions, taking into account the measured values measured by the sensor 2, which can be stored as data in the memory unit. The control instructions can be used to control the modulator 4.

The modulator 4 can be controlled in particular in such a way that the energy output is constant and independent of the signal form. In particular, the modulator 4 can be controlled in such a way that any desired signal form is generated in the modulator 4, typically a combination of amplitude and frequency modulation can take place. According to an embodiment, the modulator 4 can be configured as a transformer. This transformer is used to generate the electrical voltage required to ionize the gas in the electrode.

The input voltage of the generator 3 can range from 8V up to and including 65V. The output voltage of the modulator 4 is transformed by means of the generator 3, for example, to an electrical voltage in the range from 5 kV up to and including 25 kV. The generator thus contains a high-voltage transformer. According to an embodiment, the high-voltage transformer is configured as a Tesla coil. The high voltage transformer includes a primary winding for receiving the power supplied by the modulator. A primary winding voltage is thus present at the primary winding, for example in the range from 8 V up to and including 65 V. The high-voltage transformer contains a secondary winding at which a secondary winding voltage can be obtained. This secondary winding voltage is greater than the primary winding voltage. The secondary winding of the high-voltage transformer configured as a Tesla coil is arranged concentrically to the primary winding, which enables the high-voltage transformer to be designed in a particularly space-saving manner. The secondary winding voltage can be at least 100 times the primary winding voltage. In particular, the secondary winding voltage can be 300 times up to and including 1000 times as large as the primary winding voltage. According to an embodiment, if the primary winding voltage is 65 V, the secondary winding voltage is 25 kV. According to this exemplary embodiment, the secondary winding voltage is 385 times higher than the primary winding voltage.

The voltage pulses generated by the modulator 4 are thus transformed into high-voltage pulses in the generator 3 and fed to the electrode 1 which contains an anode 45. The anode 45 is located in the interior of a glass body 27. The anode contains a material from which electrical charge carriers, in particular electrons and ions, can be released when a high voltage is applied. These electrical charge carriers reach the gas-filled glass body 27.

The positively charged electrical charge carriers move in the direction of the cathode 55. According to this embodiment, the cathode 55 is formed by the surface to be treated, which is shown schematically. The negatively charged electrical charge carriers move towards the anode. If the negatively charged charge carriers are sufficiently accelerated, they can release further charge carriers when they hit the anode, which can then enter the interior gas-filled space. When the electrons hit the gas molecules, ions are generated, which move towards the cathode as positive charge carriers. If the applied voltage is in the range from 5 up to and including 25 kV, the number of charge carriers in the gas increases like an avalanche, so that the gas is ionized, and a plasma is formed. In this case, a so-called cold plasma is obtained, since the electrons are not created by thermal emission, but are created as secondary electrons as a result of the contact of charge carriers with the anode material.

According to the invention, the cathode 55 is located outside the glass body 27, so the electric field built up in the electrode 1 also acts on charge carriers in the air, for example oxygen. The second end 22 of the electrode 1 has the effect of a dielectric barrier. In particular, oxygen molecules can be ionized by the applied electrical field, whereby a so-called secondary plasma is formed. In particular, when the cathode is at a distance of up to 2 mm from the second end 22 of the electrode 1, a dielectrically hindered discharge can be ignited in the air space.

In terms of its mode of operation, the therapeutic device 20 corresponds to a capacitor, the first pole of which is formed by the housing 12 and the second pole of which is formed by the body part being treated. The first pole is formed by the electrode 1 containing the anode 45. The second pole is formed by the cathode 55. According to the present embodiment, the housing 12, which contains the electrode 1, forms one of the poles of the capacitor. The person holding the housing 12 in their hand during therapy brings the housing into contact with the opposite pole of this capacitor, the part of the patient's body to be treated, or at least approaches it in such a way that a secondary plasma can form.

FIG. 1*c* shows an exploded drawing of a housing 12 in which the electrode 1, the generator 3, the modulator 4, the processor unit 5 and the energy storage unit 10 are arranged. The housing 12 contains the operating elements 5, 15 described above.

According to an embodiment, the housing 12 contains an electrically conductive or conductable surface, for example a conductive plastic or a plastic coated with an electrically conductive material.

The energy delivered via the electrode 1 can be used for cell stimulation or cell therapy.

Figure 2:
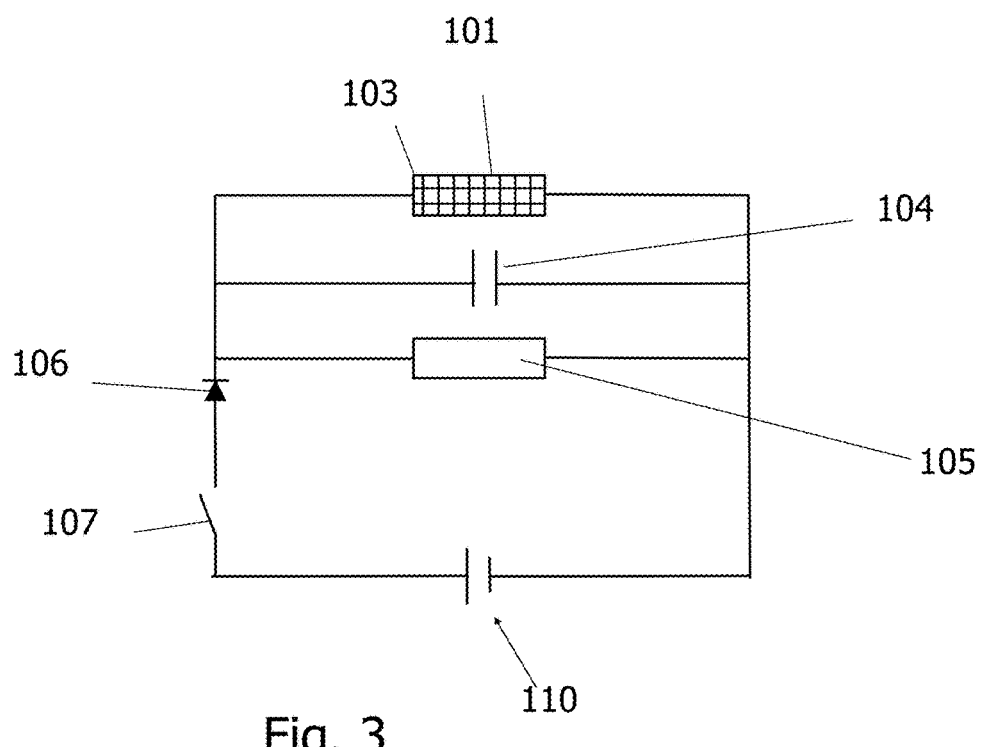

FIG. 2 shows a simplified diagram of the therapeutic device according to EP 2397187 A1. This previously known therapeutic device is powered by a direct current source 110, for example a battery. A current flows from the capacitor 104 to the coil 103, which induces an electromagnetic field when the connection to the direct current source 110 is interrupted by means of the switch 107. According to this embodiment, the coil is the potential-generating element for an electrode 101. A potential difference is generated by the coil. Due to the potential difference, an electrical voltage is present at the electrode 101. This electrical voltage is transmitted to the patient by means of the electrode 101 which is in contact with the patient. A diode 106 prevents current from flowing back into the battery circuit. If the switch 107 is closed, the capacitor 104 can be charged by the battery 110 in turn. Since the coil 103 acts as an electrical resistance in this circuit, the capacitor 104 is charged, and there is no potential difference at the electrode 101. Due to the periodic opening and closing of the switch 107, the potential difference at the electrode 101 can fluctuate between the value zero and the maximum value that can be generated by the built-in coil 103, so that pulsed operation is made possible. As a result, a pulsed electrical voltage is generated that can be used for therapeutic purposes. The direction of the current flowing to the capacitor when the switch 107 is open is opposite to the direction of flow when the switch 107 is closed. The diode 106 prevents the current from flowing back into the battery circuit when switch 107 is closed. The frequency of the pulsed electrical voltage is thus determined by the switching frequency of switch 107. A pulsed voltage of variable frequency can thus be generated with this therapeutic device, although the amplitude of the voltage is predetermined by the coil 103 used. The bleeder resistor 105 connected in parallel with the capacitor 104 is a component to prevent electric shocks when the therapeutic device is touched after the direct current source has been switched off. The capacitor 104 can be discharged via the bleeder resistor 105.

Figure 3:
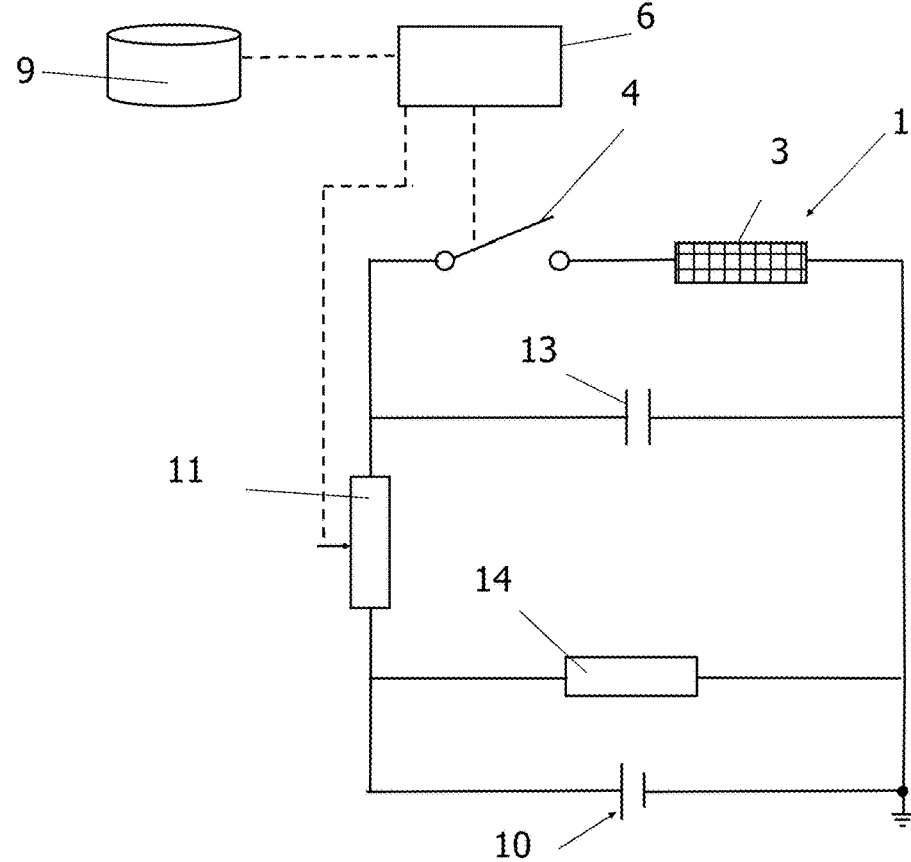

FIG. 3 shows a circuit diagram of the therapeutic device according to the invention in a simplified form. The therapeutic device includes a generator 3, which is configured as a coil, by means of which a pulsed voltage can be generated, which is directed by means of the electrode 1 to the part of a patient's body to be treated. The pulse frequency and the pulse duration can be adjusted by means of the modulator 4, which is configured as a switch according to the present embodiment. When the switch is closed, the capacitor 13 can discharge through the coil. This means that an electrical voltage is applied to the coil, so that an electromagnetic field is created, which produces the desired therapeutic effect on the body cells in its neighboring region. The amperage can be adjusted using the potentiometer 11. As a result, the amplitude of the voltage applied to the coil can be changed.

When the switch is in the open position as shown in the present illustration, no current can flow through the coil, i.e., the coil does not generate an electromagnetic field. The capacitor 13 can be charged by the energy storage unit 10, that is, according to this embodiment, by the direct current source. As in the prior art, the bleeder resistor 14 connected in parallel with the capacitor 13 is a component for preventing electric shocks when the therapeutic device is touched after the direct current source has been switched off. The capacitor 13 can be safely discharged via the bleeder resistor 14.

FIG. 4a shows a possible voltage curve over time for the known therapeutic device shown in FIG. 2. The graphic representation in FIG. 4a shows the electrical voltage as a function of time, i.e., the electrical voltage in volts is entered on the ordinate and the time on the abscissa. Voltage pulses can be generated by means of the previously known therapeutic device by opening the switch 107 for a short period of time and then closing it again, so that the coil is supplied with current as long as the switch is closed, but the current supply is interrupted as long as the switch is open. For example, the switch can be closed for about 1 ms, then opened for 1 ms. As long as the switch is closed, a voltage is built up by the current flowing through the coil. As long as the switch is open, no voltage is generated. This means that the time during which the switch is closed corresponds to a voltage pulse. If the switch is opened and closed again several times, a plurality of voltage pulses can be generated, which is shown in FIG. 4a as an example for five voltage pulses. Thereafter, the switch can be opened for a longer period of time. No voltage is generated during this period of time because no current can flow through the coil. This period of time can be of any length. If the treatment requires it, a further series of voltage pulses can be generated by opening and closing the switch again several times for a short period of time.

FIG. 4b shows a possible frequency response over time of the known therapeutic device shown in FIG. 2. The frequency in Hertz is entered on the ordinate and the time on the abscissa. Each series of voltage pulses in FIG. 4a corresponds to a frequency greater than zero, which is shown as a column in FIG. 4b. As long as the switch 107 is open, no voltage is generated since no current flows through the coil. Therefore, the frequency during this period is zero Hertz.

FIG. 5a shows a possible voltage profile over time of the therapeutic device shown in FIG. 3 according to an embodiment of the invention. The graphic representation in FIG. 5a shows the electrical voltage as a function of time, i.e., the electrical voltage in volts is entered on the ordinate and the time on the abscissa. Voltage pulses can be generated by means of the therapeutic device by actuating modulator 4, e.g., opening the switch for a short period of time and then closing it again, so that the coil is supplied with current as long as the switch is closed, but the current supply is interrupted, as long as the switch is open.

For example, the switch can be closed for about 1 ms, then opened for 1 ms. The switch can also be opened for 0.1 s and closed for 0.1 s. The range in which the opening time can vary can be, in particular, 0.001 s up to and including 0.1 s. The range in which the closing time can vary can be, in particular, 0.001 s up to and including 0.1 s. As long as the switch is closed, a voltage is built up by the current flowing through the coil. As long as the switch is open, no voltage is generated. This means that the time during which the switch is closed corresponds to a voltage pulse. If the switch is opened and closed again several times, a plurality of voltage pulses can be generated, which is shown in FIG. 5a by way of example for 13 voltage pulses which form a voltage pulse sequence. Thereafter, the switch can be opened for a longer period of time. No voltage is generated during this period of time because no current can flow through the coil. This period of time can be of any length. For example, the period of time can be in the range from 0.1 s up to and including 10 s. The period of time can in particular be in the range from 0.1 s up to and including 1 s. According to an embodiment, the time span can be 0.1 s. If the treatment requires it, at least one further sequence of voltage pulses can be generated by repeatedly opening and closing the switch again for a short period of time. Two voltage pulse sequences are shown as an example in FIG. 5a.

For each of the voltage pulse sequences of n voltage pulses illustrated in FIG. 5a the voltage of each voltage pulse increases during a period of time $t_2$-$t_1$ or $t_6$-$t_5$, the voltage of each voltage pulse remains constant during a period of time $t_3$-$t_2$ or $t_7$-$t_6$ and the voltage of each voltage pulse decreases during a period of time $t_4$-$t_3$ or $t_8$-$t_7$. The average pulse duration $t_m$ of n voltage pulses corresponds to (t4-t1)/2n if the period of time in which the switch is switched on corresponds to the period of time in which the switch is switched off.

If the duration is of each of the n voltage pulses differs from the duration tp of each of the pause times between the voltage pulses, the mean pulse duration tm of n voltage pulses and m pause times can be determined as follows. The duration of the voltage pulse sequence D corresponds to the sum over all tsi and the sum over all tpi. The i-th periods of time of each of the voltage pulses 1 to n are denoted by tsi. The i-th periods of time of each of the pause times from 1 to m are denoted by tpi. The i-th voltage pulse extends, for example, over a period of time tsi, and the (i+1)-th voltage pulse extends over a period of time ts(i+1). The i-th pause time has a period of time tpi, for example, and the (i+1) th pause time has a period of time tp(i+1). In order to obtain the average pulse duration tm, the duration of the voltage pulse sequence D is divided by the number (n+m) of voltage pulses and pause times, where n corresponds to the number of voltage pulses and m to the number of pause times in a sequence of voltage pulses.

Therefore, according to the present embodiment, the amplitude of the voltage pulses varies. According to FIG. 5a, the amplitude of the voltage pulses increases within the period of time t2-t1. The amplitude of the voltage pulses remains constant during the period of time t3-t2. The amplitude of the voltage pulses decreases during the period of time t4-t3.

FIG. 5b shows a possible frequency response over time of the therapeutic device shown in FIG. 3 according to an embodiment of the invention. The frequency in Hertz is entered on the ordinate and the time on the abscissa. Each sequence of voltage pulses in FIG. 5a corresponds to a frequency greater than zero, which is shown as a trapezoidal body in FIG. 5b. As long as the switch is opened, no voltage is generated because no current flows through the coil. Therefore, the frequency during this period of time between two adjacent voltage pulse sequences is zero hertz. According to FIG. 5b, the frequency of the voltage pulses of the first voltage pulse sequence increases within the period of time t2-t1. The frequency of the voltage pulses remains constant during the period of time t3-t2. The frequency of the voltage pulses decreases during the period of time t4-t3. The frequency of the voltage pulses of the second voltage pulse sequence also increases within the period of time t6-t5. The frequency of the voltage pulses remains constant during the period of time t7-t6. The frequency of the voltage pulses decreases during the period of time t8-t7.

In this regard, the illustration according to FIG. 5a does not correlate with the illustration according to FIG. 5b. According to FIG. 5a, the duration of the voltage pulses remains constant, so the corresponding frequency would be constant in a graphic representation corresponding to FIG. 5b.

According to the variant shown in FIG. 5b, the period of time tsi thus decreases within the period of time t2-t1, the period of time tsi is constant within the period of time t3-t2. The period of time tsi increases within the period of time t4-t3.

For the second voltage pulse sequence shown in FIG. 5b, the period of time tsi thus decreases within the period of time t6-t5, the period of time tsi is constant within the period of time t7-t6. The period of time tsi increases within the period of time t8-t7.

Figures 6A, 6B, 6C, 6D, 6E:
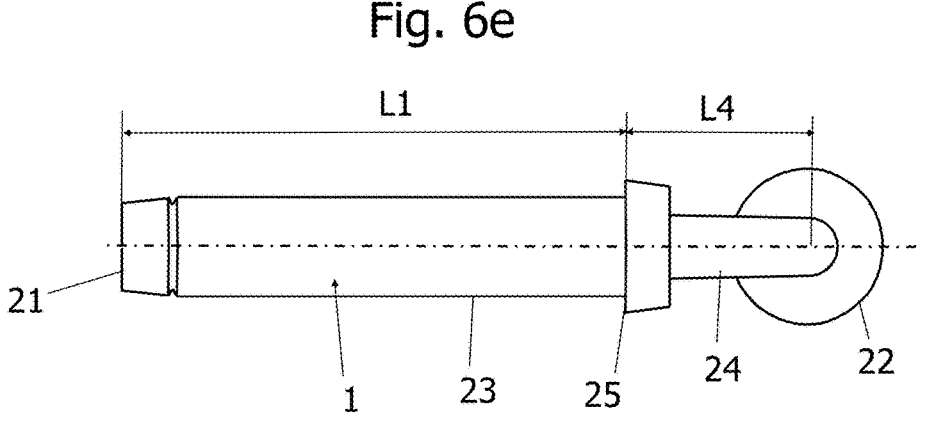
FIG. 6a: a first portion of a two-part housing for a therapeutic device of FIG. 1b or FIG. 1c, FIG. 6b: a view of a first variant of an electrode for a therapeutic device according to FIG. 1b or FIG. 1c, FIG. 6c: a second portion of a two-part housing for a therapeutic device of FIG. 1b or FIG. 1c, FIG. 6d: a view of a second variant of an electrode.
FIG. 6e: a view of a third variant of an electrode.

FIG. 6a shows a first portion 17 of a two-part housing 12 of a therapeutic device 20.

FIG. 6b shows an embodiment of a first variant for an electrode 1 located in the housing 12. The electrode 1 can thus be removed from the housing 12 and, if necessary, replaced by another electrode. The electrode 1 comprises a first section 23 and a second section 24, the first section 23 having a length L1 and the second section 24 having a second length L2. The first section 23 extends from a first end 21 to a stop element 25. The second section 24 extends from the stop element 25 to a second end 22 of the electrode 1.

FIG. 6c shows a second portion 18 of the two-part housing 12.

FIG. 6d shows an embodiment of a second variant of an electrode 1. According to the variant illustrated in FIG. 6d, the length L3 of the second section 24 is greater than the length L2 of the corresponding second section 24 according to FIG. 6b. The length L1 of the first section corresponds to the length L1 according to FIG. 6b since the electrode 1 according to the second variant can be built into the housing 12 instead of the electrode 1 according to the first variant.

FIG. 6e shows an embodiment of a third variant of an electrode 1. According to the variant illustrated in FIG. 6e, the length L4 of the second section 24 is greater than the length L2 of the corresponding second section 24 according to FIG. 6b, but smaller than the length L3 of the second section 24 of the electrode according to the second variant. This embodiment also shows only an exemplary configuration. Of course, the length L4 can deviate from the present illustration. The length L1 of the first section corresponds to the length L1 according to FIG. 6b since the electrode 1 according to the third variant can be built into the housing 12 instead of the electrode 1 according to the first variant. The second end 22 of this electrode 1 is not formed as a rounded tip as shown in the previous embodiments but includes an end which is formed like a flange. This electrode 1 is used when a gas discharge is to extend over a larger area on an object to be treated, according to the present illustration over the circular area. A first end 21 is also shown in the second and third variants of the electrode 1 depicted in FIG. 6d and FIG. 6e.

Figure 6F:
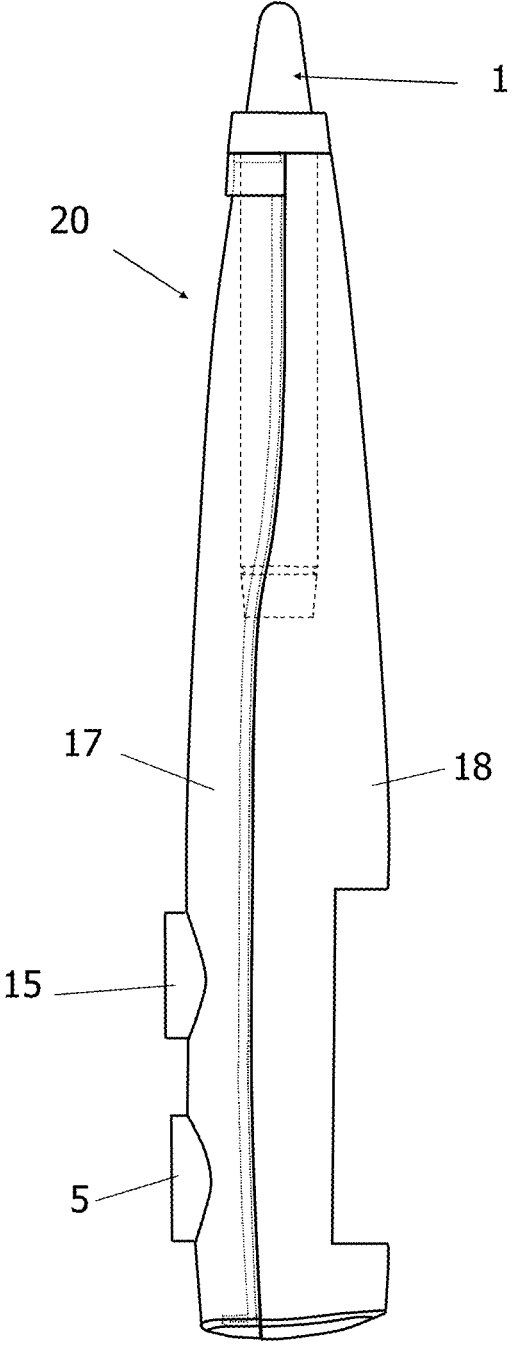
FIG. 6f: a view of a therapeutic device of FIG. 1b or FIG. 1c, FIG. 6g: a longitudinal section of a fourth variant of an electrode.

FIG. 6f shows the therapeutic device 20 containing a housing according to FIGS. 6a and 6c and an electrode 1 according to one of the variants shown in FIGS. 6b, 6d, 6e, which comprises a two-part housing 12 in which an electrode 1 can be arranged. The electrode 1 is replaceable. In order to replace the electrode 1, the first portion 17 of the housing 12 and the second portion 18 of the housing 12 can be separated from one another.

Figure 6G:
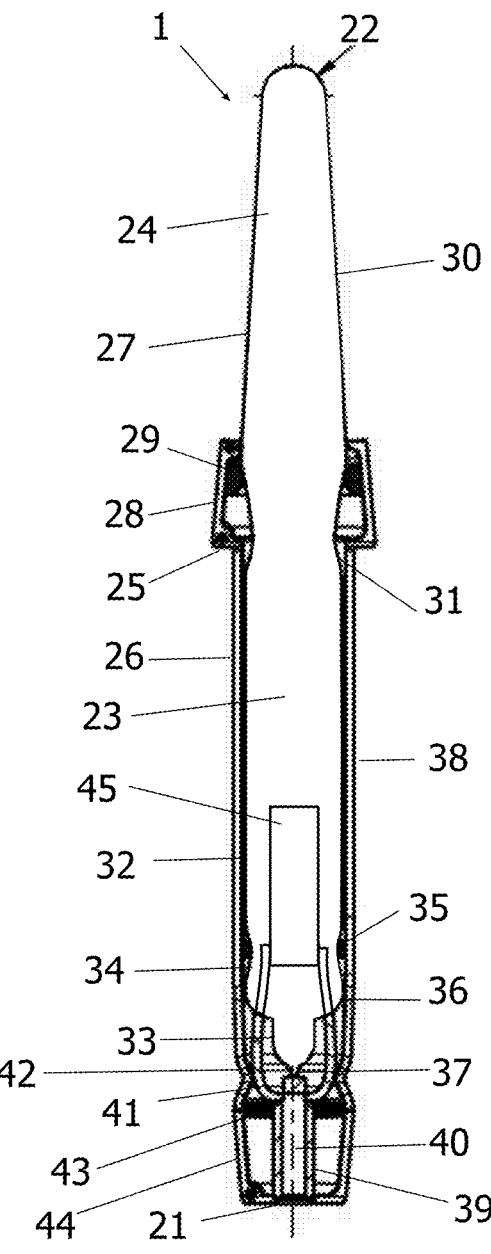

FIG. 6g shows an embodiment of a fourth variant of an electrode 1, which is shown in a longitudinal section. The electrode 1 has a first end 21 which is configured for coupling to the modulator 4. The electrode 1 has a second end 22 which is configured as a rounded tip. The electrode 1 comprises a glass body 27 which is arranged in a holding element 26 in such a way that at least the second end 22 protrudes beyond the holding element 26. The holding element 26 extends in the assembled state in the housing up to the stop element 25. According to this embodiment, the stop element 25 is part of a conical end section 28. In the interior of the conical end section 28 there is a bearing element 29, which supports the glass body 27 in the holding element 26.

The glass body 27 includes a conical section 30 which extends from the second end 22 to the conical end section 28. The diameter of the conical section can increase continuously from the second end 22 to the conical end section 28. In the region of the conical end section 28, the glass body 27 contains a constriction 31, i.e., its diameter decreases in the area of the conical end section 28, in order to then widen again to a larger diameter in the middle section 38 adjoining the conical end section 28. The outside diameter of the glass body 27 in the middle section 38 can essentially correspond to the inside diameter of the middle section 38 of the holding element 26. The section of the glass body 27 which is of essentially cylindrical design will be referred to as the central section 32 subsequently.

An end section 33 of the glass body 27 which includes a groove 34 and a coupling element 36 with a tip 37 adjoins the central section 32. A sealing element 35 is located in the groove 34 and rests against the inner wall of the middle section 38 of the holding element 26.

A pin element 40 extends from the tip 37 to the first end 21 of the electrode. The pin element 40 is connected to a conductor element 39 which is provided with electrical conductivity so that the voltage pulses generated by the modulator 4 and transformed to the high voltage by the generator 3 can be transmitted to the glass body 27 and to the gas located therein. The pin element 40 is connected to the conductor element 39 which extends from the pin element 40 to an arcuate element 41. The conductor element 39 can be configured, for example, as a wire or as a sleeve. According to this embodiment, the arcuate element 41 is part of the conductor element 39. The pin element 40 and the conductor element 39 are electrically insulated from the environment by the holding element 26. The holding element 26 contains or consists of a non-electrically conductive material, for example a plastic. The conductor element 39 penetrates the jacket of the glass body 27 and leads into the interior of the glass body 27 to an anode 45 arranged there.

In addition, the pin element 40 is positioned and centered in its axial position by a positioning element 43, so that it is ensured that the axis of the pin element 40 is aligned with the central axis of the glass body 27, i.e., the pin element 40 is arranged coaxially to the glass body 27. The sleeve 39 is located inside the end section 44 of the holding element 26 adjoining the groove 42. An annular cavity is formed between the sleeve 39 and the end section 44.

Figure 7:
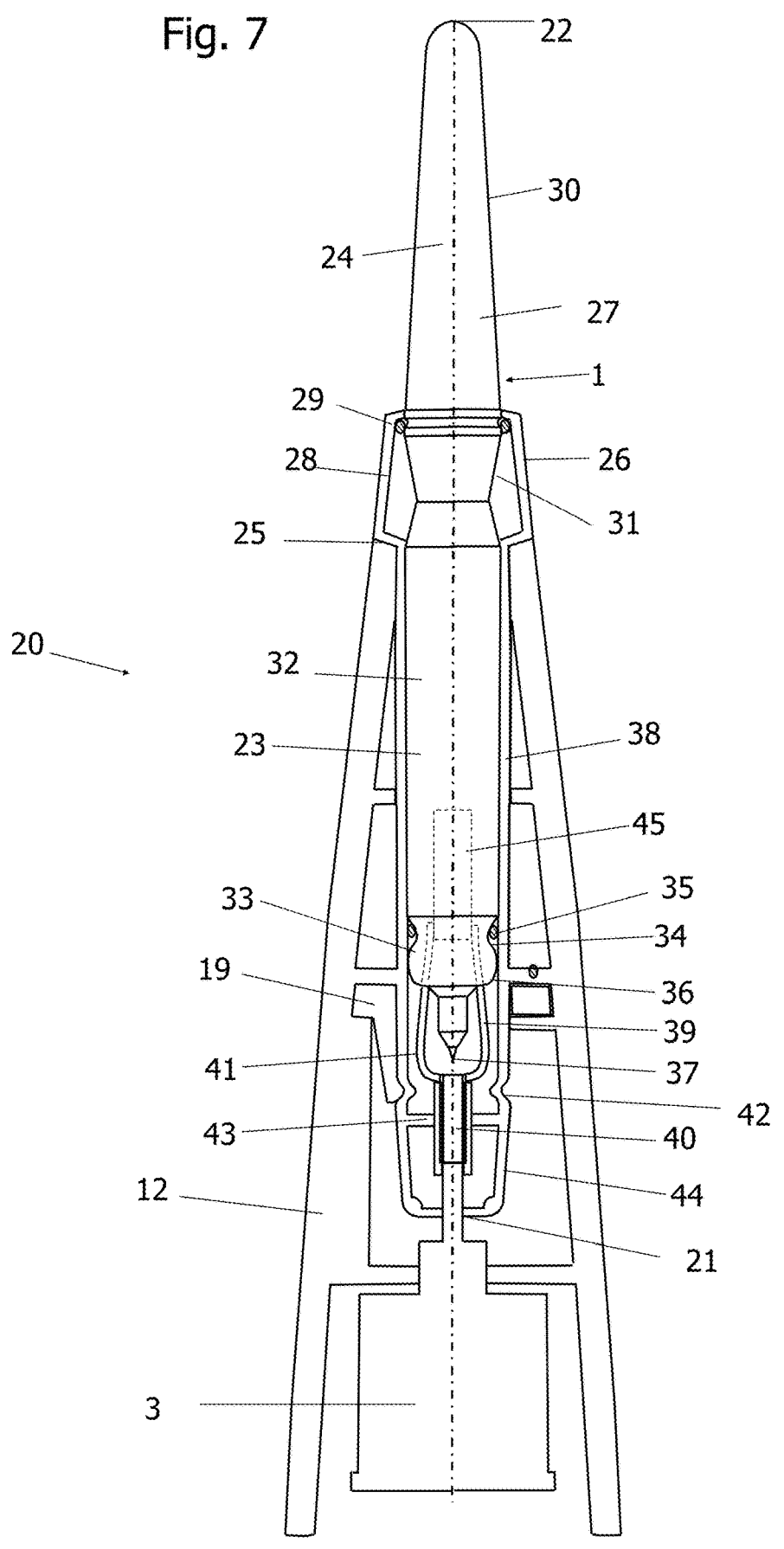
FIG. 7: a partial section through the housing with the electrode of a therapeutic device of FIG. 1b or FIG. 1c arranged therein.

FIG. 7 shows a partial section of a therapeutic device 20 in which an electrode according to FIG. 6g is accommodated in the housing 12. The electrode 1 is held in the housing 12 by means of a snap-in connection 19. The end of the housing 12 is positioned on the stop element 25 so that the electrode 1 is held in the desired position in the housing.

In FIG. 7 also shows an embodiment for the electrical coupling of the electrode 1 to the generator 3, which can be configured in particular as a Tesla coil. The generator 3 contains a connection element which is in contact with the pin element 40. The pin element 40 contains an electrically conductive material so that the electrical high voltage generated by the generator 3 can be transmitted via the pin element 40 to the conductor elements 39 leading to the anode 45. A spring element may be provided to ensure the contact between the pin element and the terminal element.

Figures 8A, 8B:
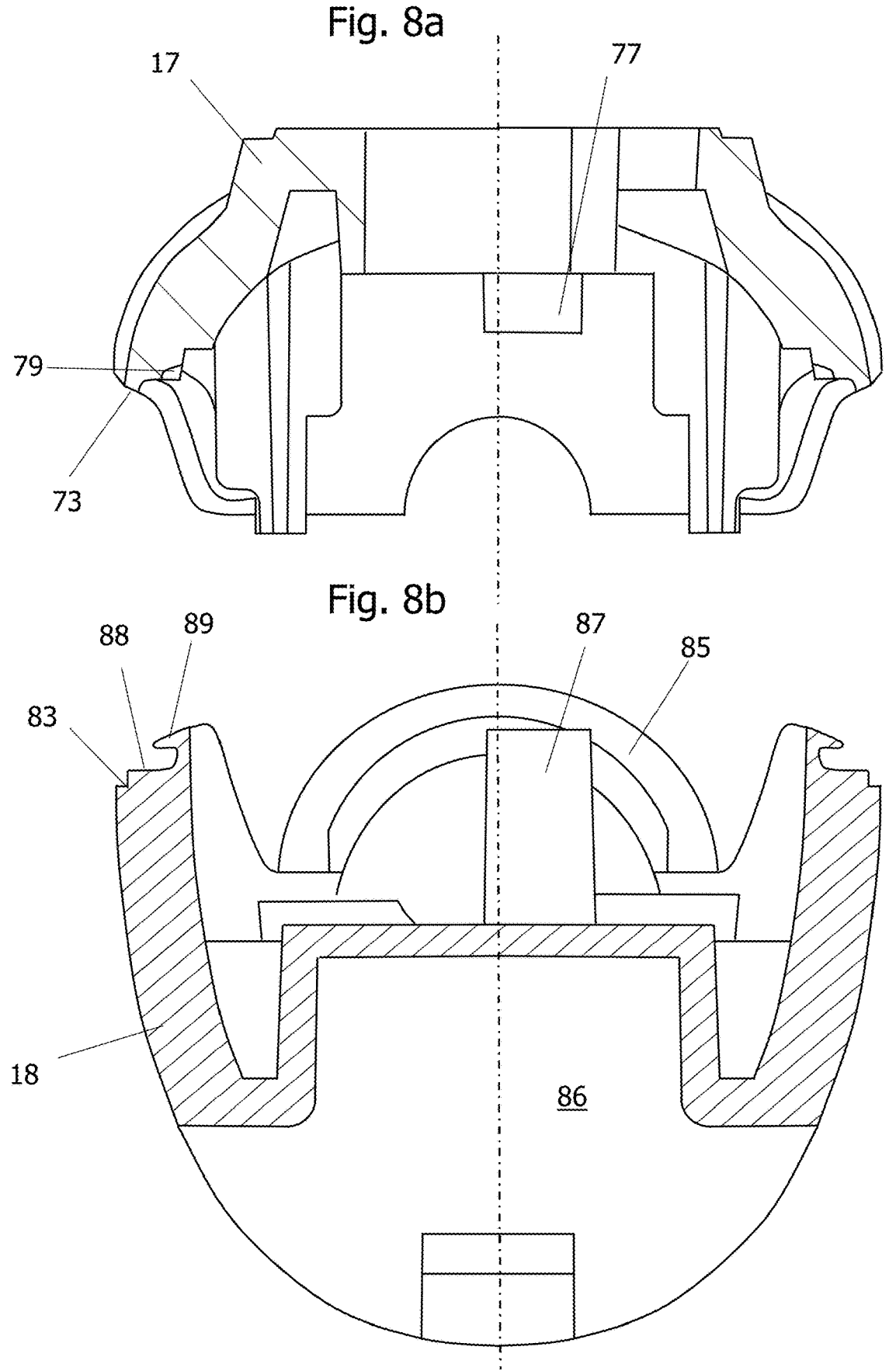
FIG. 8a: a radial section through the first portion of the housing of FIG. 6a FIG. 8b: radial section through the second portion of the housing of FIG. 6c, FIG. 9: a measuring arrangement for measuring a patient leakage current, FIG. 10a a graph of the patient leakage current as a function of the distance of a first therapeutic device from the cathode, FIG. 10b a graph of the patient leakage current as a function of the distance of a second therapeutic device from the cathode, FIG. 10c a graph of the patient leakage current as a function of the distance of a third therapeutic device from the cathode, FIG. 10d the temperature profile as a function of the distance between the electrode and the cathode for the second therapeutic device FIG. 11 a measuring arrangement for determining the composition of a secondary plasma generated by means of the therapeutic device, FIG. 12a a graph of the composition of the secondary plasma of the first therapeutic device, FIG. 12b a graph of the composition of the secondary plasma of the second therapeutic device, FIG. 12c a graph of the composition of the secondary plasma of the third therapeutic device, FIG. 13 a spectrum of the third therapeutic device compared to the first therapeutic device, FIG. 14 a measuring arrangement for determining the reactive species formed during the discharge, FIG. 15 an exemplary spectrum of the first therapeutic device determined by means of FTIR spectroscopy, FIG. 16 a plot of the measured current at the HI setting, FIG. 17a the pH value as a function of the treatment time for a first therapeutic device at the setting LO, FIG. 17b the pH value as a function of the treatment time for the first therapeutic device at the setting HI, FIG. 17c the pH value as a function of the treatment time for the second therapeutic device in water, FIG. 17d the pH value as a function of the treatment time for the second therapeutic device in NaCl, FIG. 17e the pH value as a function of the treatment time for a first electrode of the third therapeutic device in water, FIG. 17f the pH value as a function of the treatment time for a second electrode of the third therapeutic device in water, FIG. 18a the concentration of $H_2O_2$ as a function of the treatment time for the first therapeutic device, FIG. 18b the concentration of $H_2O_2$ in water for the second therapeutic device, FIG. 18c the concentration of $H_2O_2$ in NaCl for the second therapeutic device, FIG. 19 the concentration of $NO_2^-$ in $H_2O$ and NaCl as a function of the treatment time for the first therapeutic device, FIG. 20 results of an MTT test to determine the cytotoxicity for the first therapeutic device, FIG. 21 results of an MTT test to determine the cytotoxicity for the second therapeutic device, FIG. 22a results of an MTT test to determine the cytotoxicity for the first electrode of the third therapeutic device, FIG. 22b results of an MTT test to determine the cytotoxicity for the second electrode of the third therapeutic device, FIG. 23 an illustration of the agar plates for an inhibition zone test for the LSE electrode for the bacterium *Staphylococcus aureus*, FIG. 24 a bar graph of the results of the inhibition zone test for the bacterium *Staphylococcus aureus* for the LSE electrode, FIG. 25 an illustration of the agar plates for an inhibition zone test for the EWC electrode of the first therapeutic device for the bacterium *Staphylococcus aureus*, FIG. 26 an illustration of the agar plates for an inhibition zone test for the EWC electrode of the first therapeutic device for the bacterium *Staphylococcus epidermidis*, FIG. 27 an illustration of the agar plates for an inhibition zone test for the EWC electrode of the first therapeutic device for the bacterium *Escherichia coli*, FIG. 28 an illustration of the agar plates for an inhibition zone test for the EWC electrode of the first therapeutic device for the bacterium *Pseudomonas aeruginosa*, FIG. 29 an illustration of the agar plates for an inhibition zone test for the EWC electrode of the first therapeutic device for the yeast *Candida albicans*, FIG. 30 a bar graph of the results of inhibition zone tests for all microorganisms for the EWC electrode of the first therapeutic device, FIG. 31 an illustration of the agar plates for an inhibition zone test for the EWC electrode of the second therapeutic device for the bacterium *Staphylococcus aureus,*

FIG. 8a shows a radial section through the first portion 17 of the housing 12, the radial section being taken along the section plane labeled A-A in FIG. 6a. The first portion 17 is provided with an edge 73 which is configured to rest on a shoulder 83 of the second portion 18. The edge 73 extends from the first end 71 of the first portion 17 to the second end 72 of the first portion 17, see also FIG. 6a.

The edge 73 contains at least one recess between the first end 71 and the second end 72, which is not visible in FIG. 6a since it is located on the inside of the housing.

FIG. 8b shows a radial section through the second portion 18 of the housing 12, which is taken along the section plane labeled B-B in FIG. 6c. A shoulder 83 extends from the first end 81 of the second section 18 to the second end 82 of the second section 18, see also FIG. 6c.

The second section 18 contains at its second end 82 a ring element 84 which is configured to receive the second end 72 of the first portion 17. In the assembled state, the electrode 1 is accommodated inside the ring element 84.

At its first end, the second portion 18 according to the present embodiment contains a latching element 85 which is configured to be received in a corresponding recess in the first portion 17. The recess is located at the first end 71 of the first portion 17 on the inside of the end wall. It is not visible in FIG. 6a and also not visible in FIG. 8a since it lies in front of the section plane, i.e., in this illustration, it belongs to the cut-away part of FIG. 8b.

The section plane in FIG. 8b runs through the receiving opening for the charging device 16, which can be detachably attached to the underside of the second portion. The electrode 1, the modulator 4, the generator 3, the processor unit containing a control, regulation, and calculation module, optionally the memory unit 9 and the associated connections and connecting lines are located on the side of the second portion 18 opposite the receiving opening 86, which are shown schematically in FIG. 1b or 1c.

The first portion 17 and the second portion 18 can also be secured by means of a screw connection. For this purpose, the first portion contains a socket 77 which contains a threaded bore, not shown, which is aligned with a socket 87 of the second portion 18 when the first portion 17 and the second portion 18 are assembled to form the housing 12.

In FIG. 8b, an additional recess 88 is provided immediately adjacent to the shoulder 83. A hook-shaped projection 89 adjoins this recess 88. In the assembled state, this hook-shaped projection 89 engages in a corresponding recess 79 of the first portion 17. The hook-shaped projection 89 thus snaps into the corresponding recess 79, as a result of which the first portion 17 covers the second portion 18 at the connection point, so that a double wall is formed at the connection point, between which a small air gap remains. Surprisingly, a better protection against the electrical voltages is thus achieved at the connecting line, so that the person operating the device is not exposed to any danger from the applied electrical voltages.

The amplitude of the voltage pulses can be adjusted via the operating elements 5, 15, on the one hand, and the frequency of the voltage pulses, on the other hand, when operating the therapeutic device according to any one of the embodiments. According to an embodiment, the amplitude of the electrical voltage can be changed in the range of values 1 to 9. The frequency can be in the range of 10 up to and including 100 pulses per second. The most powerful setting is therefore obtained when selecting amplitude 9 and selecting 100 pulses per second. In the following measurement examples, the most powerful setting is denoted by HI. The least powerful setting is therefore obtained when selecting amplitude 1 and selecting 10 pulses per second. In the following measurement examples, the least powerful setting is denoted by LO.

Figure 16:
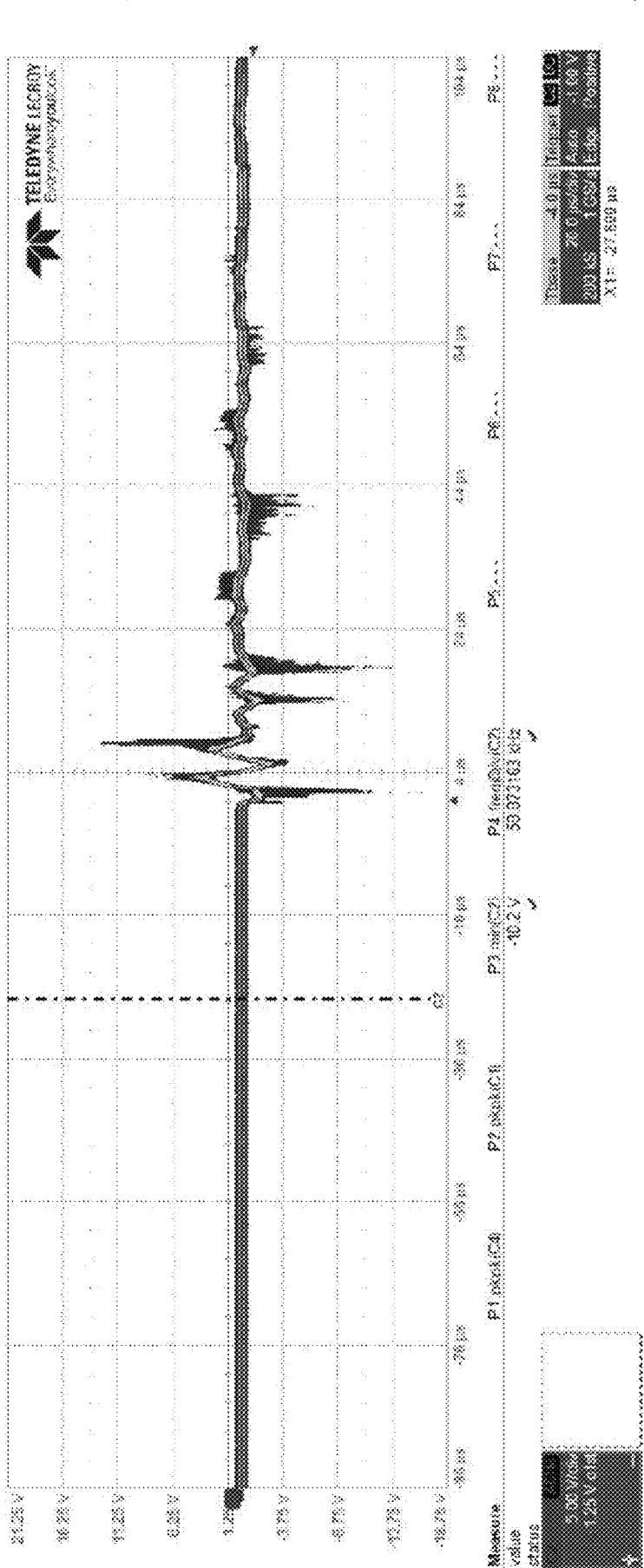

The amperage of the pulses was recorded using a Teledyne Le Croy Waverunner 8254M oscilloscope across an electrical resistor of $100\Omega$ placed between the cathode and ground at a voltage ratio of 10:1 (Teledyne Le Croy, PP024). The optimum distance D between the plasma source and the cathode was 1 up to and including 2 mm, with the cathode being formed as a copper element. For this distance, the amplitude was varied between 10 and 100 pulses/s. Pulse currents were stable and consistent with the therapeutic device specifications for all settings. In FIG. 16 (measurement example 4), the course of electrical voltage was recorded for a period of approximately 200 μs.

The effect on the stability of the plasma source was studied by adjusting the amplitude. For this purpose, the frequency of the discharge peaks in the range from 10 Hz up to and including 100 Hz was examined using the oscilloscope. Analysis of the current pulses revealed up to 12 discharges per voltage pulse at the HI settings (amplitude 9V, 100 pulses/s). The discharge operation was most stable at the highest frequency of 100 Hz and the highest amplitude, which is shown in FIG. 16.

Measurement Example 1

Figure 9:
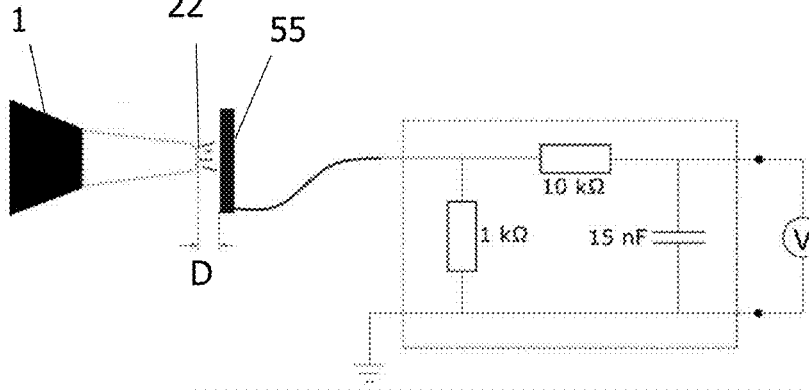

The patient leakage current (I) was determined according to the measurement specification according to DIN EN 60601-1 2]. The measurement arrangement is shown schematically in FIG. 9. The circuit shown in FIG. 9 shows a low-pass filter that describes the electrical response of the human body, particularly taking into account that currents of higher frequency are classified as less harmful. Since the therapeutic device 20 is configured as a wireless device, only an alternating current can be measured. Therefore, an R-C element containing the circuit shown in FIG. 9 was connected to a Fluke 116 True RMS multimeter to determine the patient leakage current. The measuring arrangement consists of optical holders, so that a plane parallelism between the cathode 55 and the second end 22 of the electrode 1, which forms the tip of the plasma source, is ensured. The distance was precisely set using a micrometer screw. The patient leakage current was thus measured as a function of the distance D between the second end 22 of the electrode 1 and the cathode 55, which is configured as a copper plate. The patient leakage current should not exceed a maximum value of 100 μA so that the therapeutic device can be used for medical purposes. The maximum value (▼), the minimum value (▲) and the mean value (●) of the patient leakage current were recorded for a period of 10 s. It was assumed here that the maximum value is decisive for assessing the applicability for medical purposes.

Figure 10A:
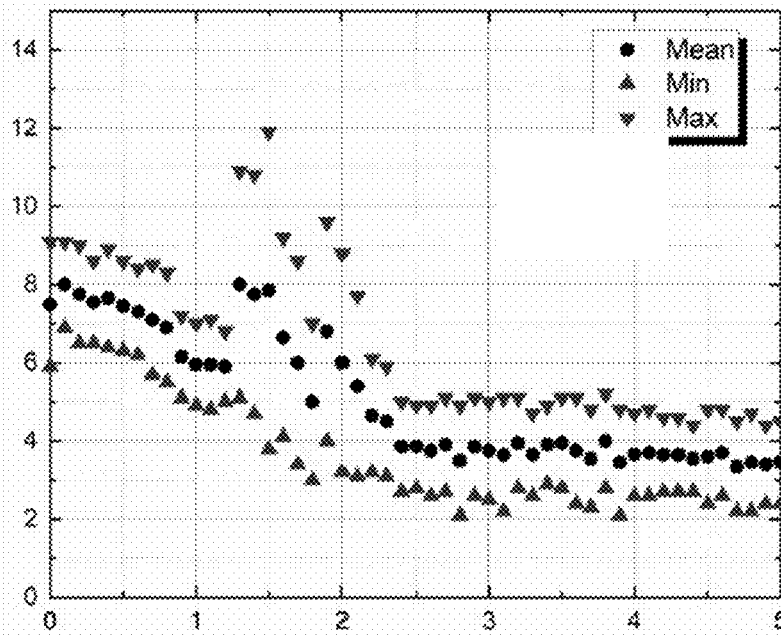

According to FIG. 10*a*, the patient leakage current for a first therapeutic device (TV1) is plotted on the ordinate in [μA], the distance D in [mm] between the second end 22 of the electrode 1 and a copper plate forming the cathode 55 is plotted on the abscissa. According to FIG. 10*a*, the limit value of 100 [μA] is not reached at any distance, even with the maximum possible settings. The maximum value reached is 12 [μA] at a distance of 1.5 mm. A filament and a stable air plasma are generated in the range from 0 to 3 mm. At greater distances, no plasma was formed, although a patient leakage current was determined. For the lowest setting (LO), no patient leakage current was detected at all.

Figure 10B:
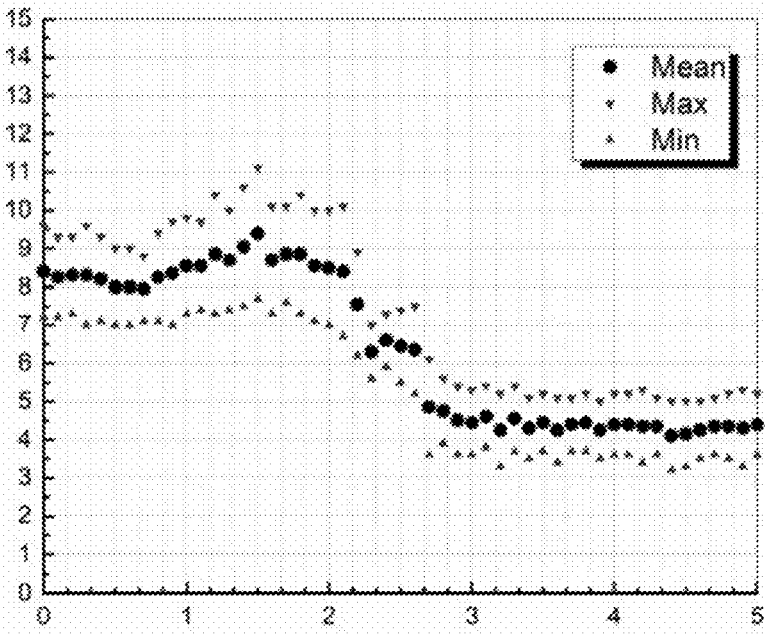

FIG. 10*b* shows the patient leakage current for a second therapeutic device (TV2). For this therapeutic device, the maximum, the minimum value, and the mean value for the patient leakage current were recorded for a period of 10 seconds at an ambient temperature of 23° C. and 45% relative humidity. The therapeutic device (TV2) showed an audible and measurable change in plasma as a function of the applied voltage. To achieve the highest intensity, the therapeutic device was wrapped in grounded aluminum foil. The maximum duration for the measurements with a single charge of the energy storage unit was 25 minutes. With two charges, failures occurred from an operating time of approx.

50 minutes, wherein the housing temperature of the second therapeutic device (TV2) reached a maximum of 43° C. With an operating time of more than 50 minutes, the increase in operating temperatures can lead to malfunctions in the processor unit, which can partially impair the operation of the control module, regulating module or calculation module of the therapeutic device. Therefore, additional measurements were carried out after a cooling phase of approx. 30 minutes after two charging cycles.

The patient leakage current of 100 μA was never reached for the second therapeutic device (TV2) either. The maximum patient leakage current was 11 μA. At a distance D of 0 up to and including 3 mm between the second end 22 of the electrode 1 and the cathode 55, a stable secondary cold plasma was generated in the air. The frequency of discharges decreased at distances greater than 2 mm, reducing patient leakage current. For the second therapeutic device (TV2), no plasma could be detected visually or audibly at a distance D>3 mm, although a low patient leakage current was measured.

Figure 10C:
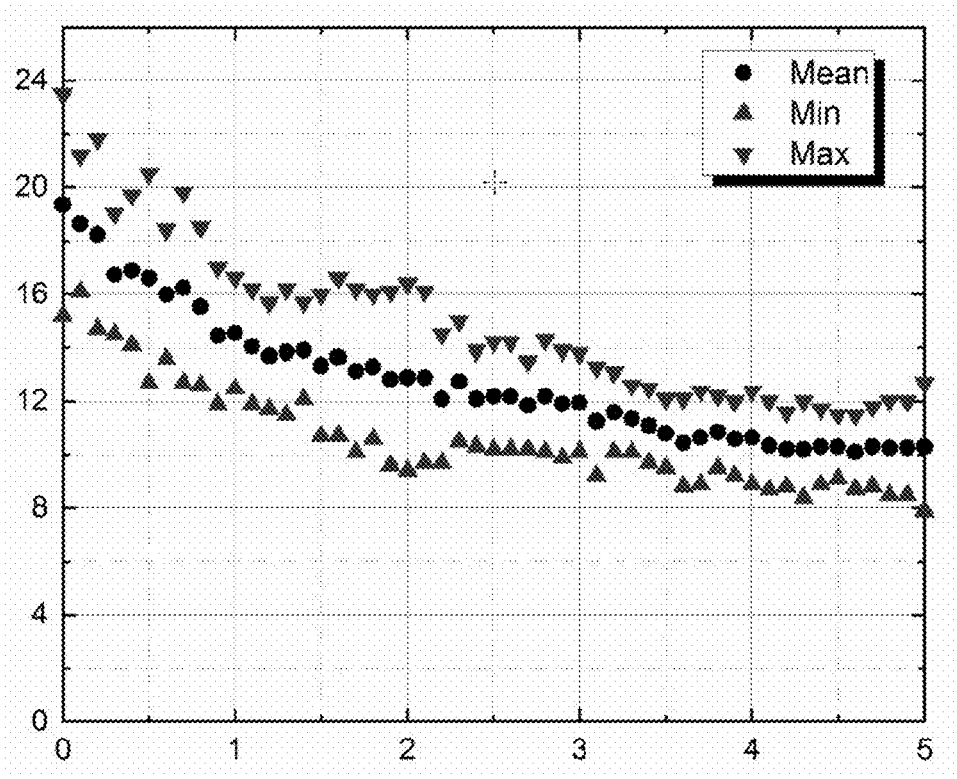

FIG. 10*c* shows the patient leakage current for a third therapeutic device (TV3) which contains an LSE electrode. For this therapeutic device, the maximum, the minimum value, and the mean value for the patient leakage current were recorded for a period of 10 seconds at an ambient temperature of 23° C. and 49% relative humidity.

The patient leakage current of 100 μA was never reached for the third therapeutic device (TV3) either. The maximum patient leakage current was 23.5 μA when the LSE electrode touches the cathode. At a distance D of 0 up to and including 3.5 mm, a stable secondary cold plasma was generated in the air between the second plate-shaped end 22 of the LSE electrode 1 and the cathode 55. The discharges became discontinuous at longer distances, although a small patient leakage current was measured.

Figure 10D:
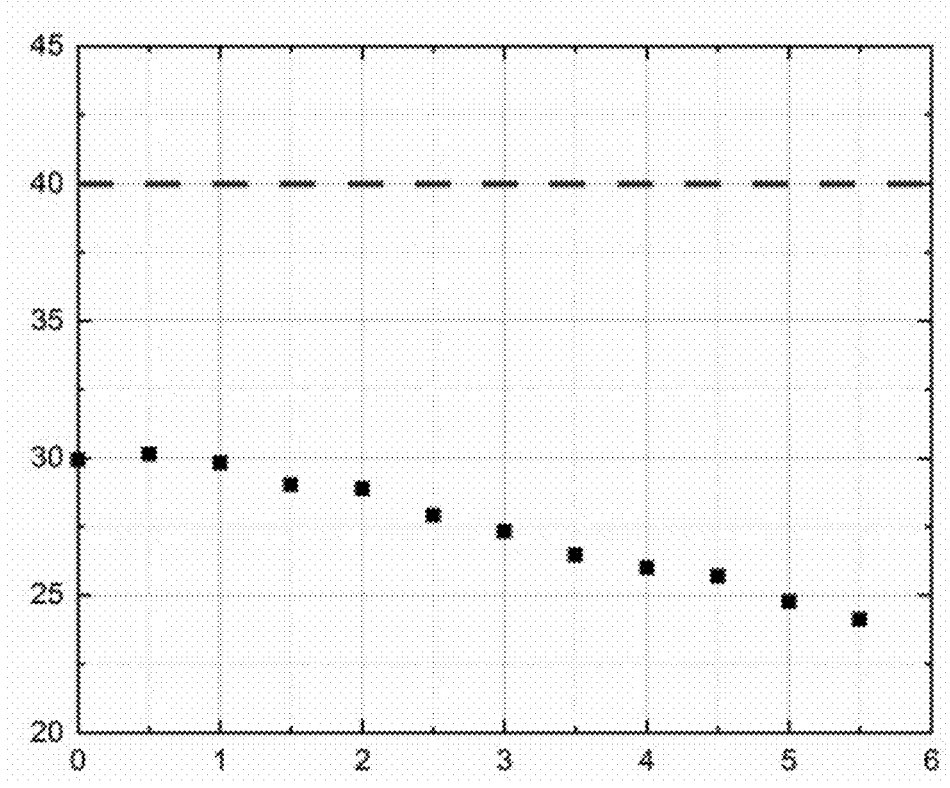

FIG. 10*d* shows the course of the temperature in degrees Celsius as a function of the distance D of the electrode from the cathode. The distance D is plotted on the abscissa and the temperature on the ordinate. At the time of the measurement, the room temperature was 23° C. with a relative humidity of 51%. For the second therapeutic device (TV2), the maximum measured temperature was 30 degrees Celsius. The limit for the temperature, which is 40 degrees Celsius, was never reached.

Measurement Example 2

Figure 11:
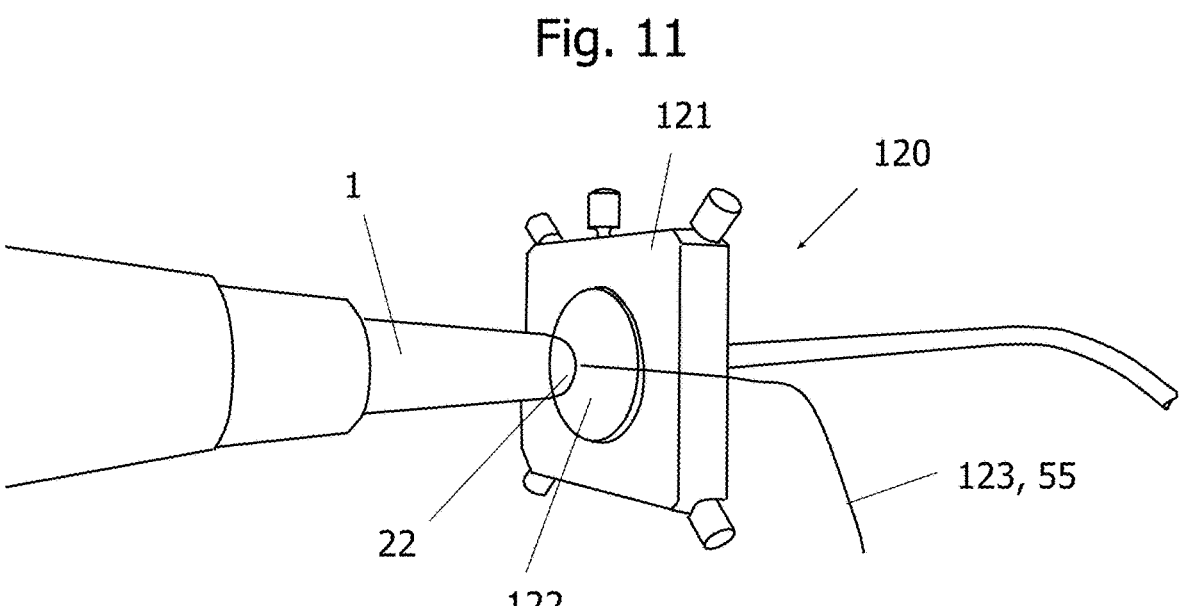

The spectral composition of the optical plasma radiation was determined using optical emission spectroscopy (OES). The corresponding measurement arrangement is shown schematically in FIG. 11. Optical emission spectroscopy was performed in the ultraviolet (UV), visible (VIS) and near infrared (NIR) regions using a calibrated AvaSpec 3648-USB2 120 fiber optic spectrometer, Avantes, Apeldoorn, NL. The plasma emission was determined using a cosine corrector 121 in order to increase the opening angle. In order to protect the cosine corrector from direct plasma contact, a quartz window 122 (d=2 mm), which is transparent for wavelengths greater than 200 nm, was attached to the side facing the electrode.

The holders required for the measuring device and the first, second and third therapeutic devices (TV1, TV2, TV3) have been omitted in the present illustration.

A grounded wire 123 served as the cathode 55. Because of the wire's small diameter of 0.1 mm, the wire 123 hardly covered the plasma light source. The distance D between the second end 22 of the electrode 1 and the cathode 55 was approximately 1.5 mm since this value corresponded to the highest patient leakage current. Five spectra were recorded and then analyzed with an integration time of 30 s for each spectrum. For medical applications, the UV irradiance is of particular interest. It was measured in two ranges, UV-A (315-380 nm) and UV-B (280-315 nm) by integrating the spectral irradiance E ($\lambda$). No emissions were detected in the UV-C range (200-280 nm).

Figure 12A:
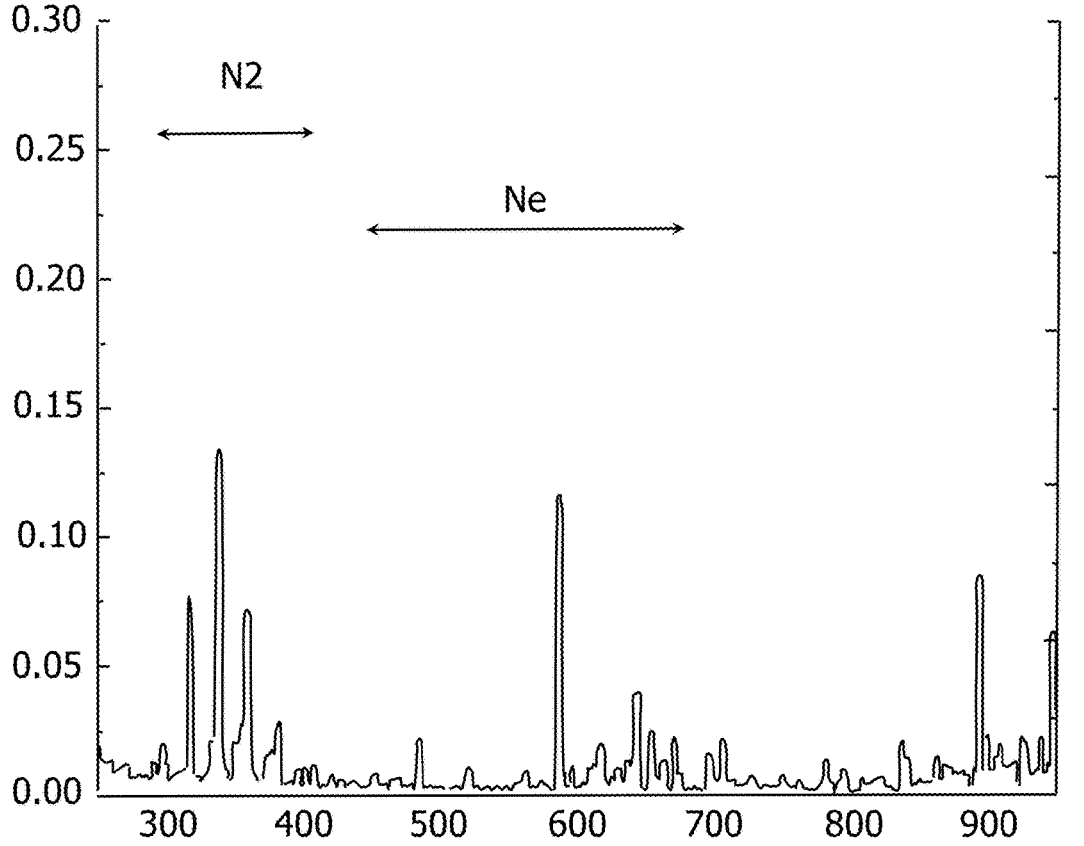

FIG. 12a shows the complete spectrum of the first therapeutic device (TV1), which was determined by forming an average value from 5 consecutive spectra with a recording time of 30 seconds each. The scale on the ordinate on the left of FIG. 12a was used for the therapeutic device (TV1). The spectrum of the therapeutic device (TV1) shows emission of neon (Ne) and nitrogen (N2). The measurements were taken at an ambient temperature of 22.7° C. and 61% relative humidity.

Figure 12B:
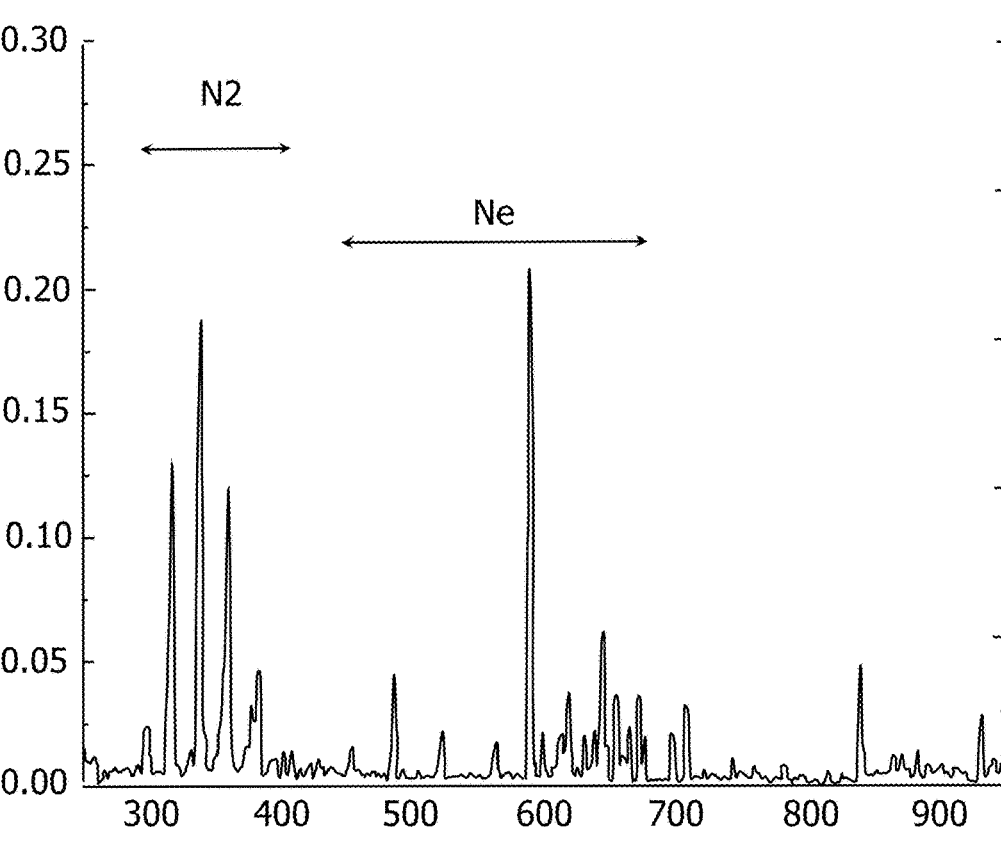

FIG. 12b shows a spectrum of the second therapeutic device (TV2). The measurements were carried out at an ambient temperature of 23° C. and 50% relative humidity, otherwise the measurement was carried out in the same way as for the first therapeutic device (TV1).

Figure 12C:
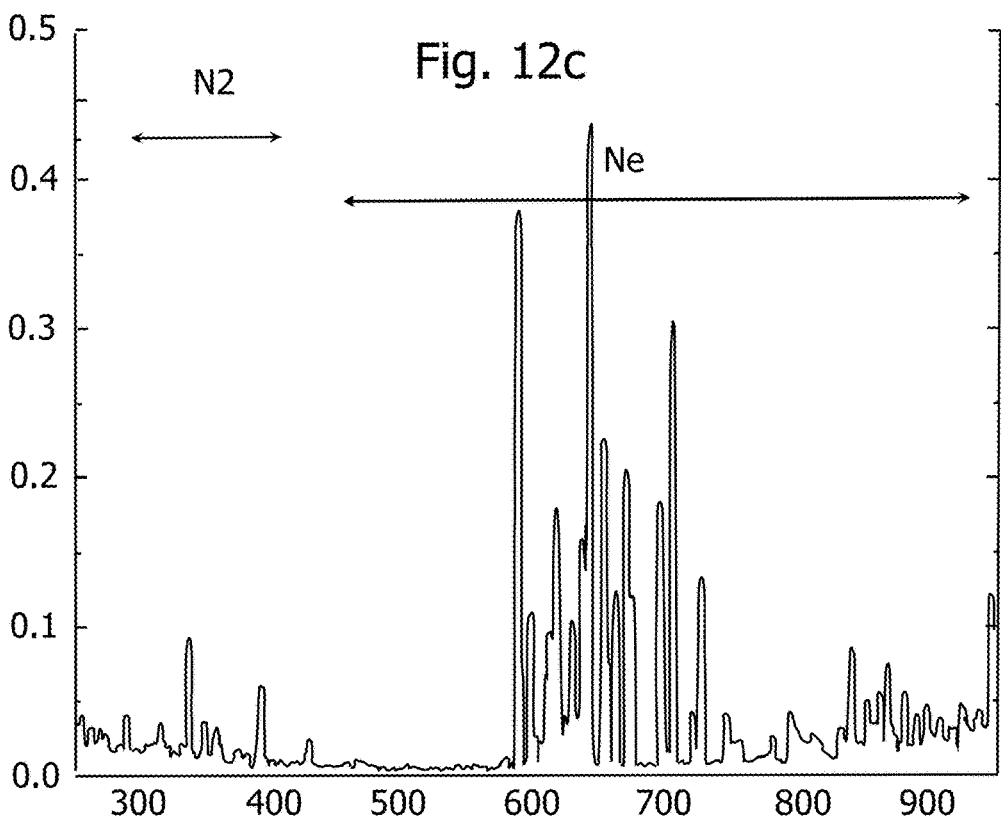

FIG. 12c shows a spectrum of the third therapeutic device (TV3). The measurements were carried out at an ambient temperature of 22.5° C. and 48% relative humidity, otherwise, the measurement was carried out in the same way as for the first therapeutic device (TV1).

Figure 13:
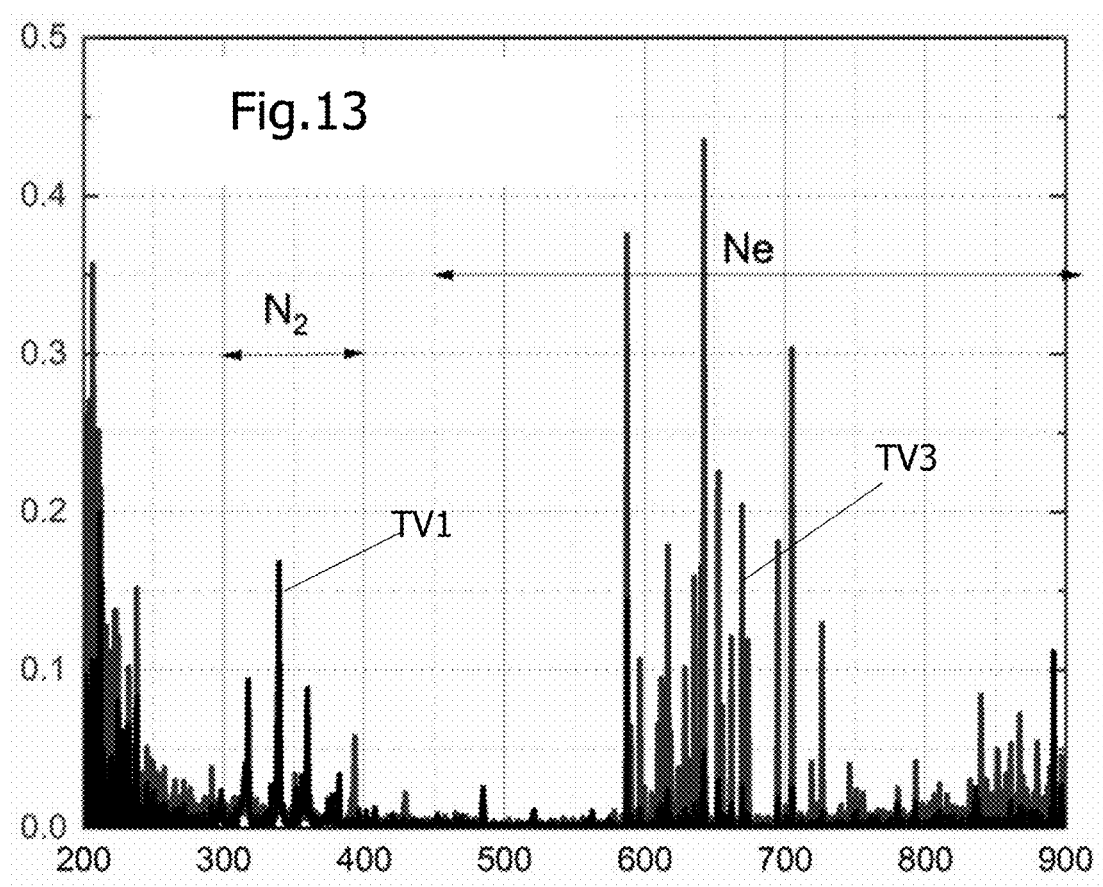

FIG. 13 shows a spectrum of the third therapeutic device (TV3) in comparison with the first therapeutic device (TV1). Compared to (TV1), the emissions of neon were higher, but lower for nitrogen. This could be explained by the larger area of glowing neon inside the LSE electrode. By means of the electrode of the first therapeutic device (TV1), due to the geometric design and the associated enlargement of the electrical field at the second end designed as a tip, a focused discharge can take place on the cathode. In contrast to (TV1), the discharges occurred at different locations on the grounded wire. Due to the positioning of the wire, the plasma could not be recorded in its entirety, therefore higher values for the nitrogen emissions result for the first therapeutic device (TV1). The irradiance in the UV-A and UV-B range and the effective irradiance of the third therapeutic device (TV3) at the measuring point with the highest intensity was compared with the values of the first therapeutic device (TV1). The irradiance levels are relatively low, as the spectrum has already indicated. The maximum daily treatment duration tmax is very high at around 1 hour. However, the UV-B values and the effective radiation intensities are higher than for the first therapeutic device (TV1). This can be related to the higher neon emission, but the measurement in the weighted regions below 300 nm can also be subject to a considerable amount of noise.

The International Commission on Non-Ionizing Radiation Protection has published a method for determining an effective irradiance, because different wavelengths cause different damage to human skin. A spectral weighting function S($\lambda$) has to be multiplied by the spectral irradiance E($\lambda$) and integrated over the entire UV range from 200 to 380 nm to calculate an effective irradiance $E_{eff}$ according to the following formula:

$$E_{eff} = \lambda_1 \int^{\lambda_2} E(\lambda) \cdot S(\lambda) d(\lambda)$$

A maximum daily exposure time $t_{max}$ can be calculated from the effective irradiance $E_{eff}$ using the maximum daily dose of $D_{max}=3$ mJ/cm$^2$ according to the following formula:

$$t_{max} = D_{max}/E_{eff}$$

The irradiance levels for UV-A and UV-B and the effective irradiance $E_{eff}$ of the first, second and third therapeutic devices (TV1, TV2, TV3) are shown in table 1 below. The irradiance levels are relatively low, as already indicated in the spectrum. There were no significant emissions in the UV-C range. The maximum daily treatment duration is very high at 6 hours for the first therapeutic device and 5 hours for the second therapeutic device.

TABLE 1

| Device, D Dimension | $E_{UV-A}$ $\mu$W/cm$^2$ | $E_{UV-B}$ $\mu$W/cm$^2$ | $E_{eff}$ $\mu$W/cm$^2$ | $t_{max}$ h |
|---|---|---|---|---|
| (TV1) 1.5 mm | 0.91 ± 0.03 | 0.19 ± 0.03 | 0.14 ± 0.2 | ~6 |
| (TV2) 1.5 mm | 1.21 ± 0.05 | 0.22 ± 0.01 | 0.16 ± 0.2 | ~5 |
| (TV3) 1.5 mm | 0.68 ± 0.04 | 0.37 ± 0.02 | 0.86 ± 0.07 | ~1 |

Measurement Example 3

In the third measurement example, FTIR spectroscopy, thus a Fourier-transformed infrared absorption spectroscopy, hereinafter referred to as FTIR, was carried out. FTIR was used to qualitatively and quantitatively determine the composition of the reactive species formed during the discharge. An absorption in the infrared range, corresponding to the excitation of molecular vibrations and rotations, is a characteristic feature of heteronuclear molecules, such as various nitrogen oxides or ozone. The determination is made by measuring a background radiation intensity $I_0$ and a radiation intensity after absorption by the sample I, both of which are dependent on the wave number v. This enables an absorption coefficient A to be determined, wherein A=−ln(I (v)/$I_0$(v))=$\Sigma_i$ ($n_i\sigma_i$(v)L. The absorption coefficient A is influenced by the length of the optical path as well as the density n and the absorption cross section $\sigma$, which depends on the wave number, for each species i. Plasma chemical processes contain complex reaction networks that occur on different time scales, hence the species composition is variable during the discharge and converges to a steady-state mixture of long-lived components in the afterglow. The measurement results shown in FIG. 15 relate to the stationary state.

Figure 14:
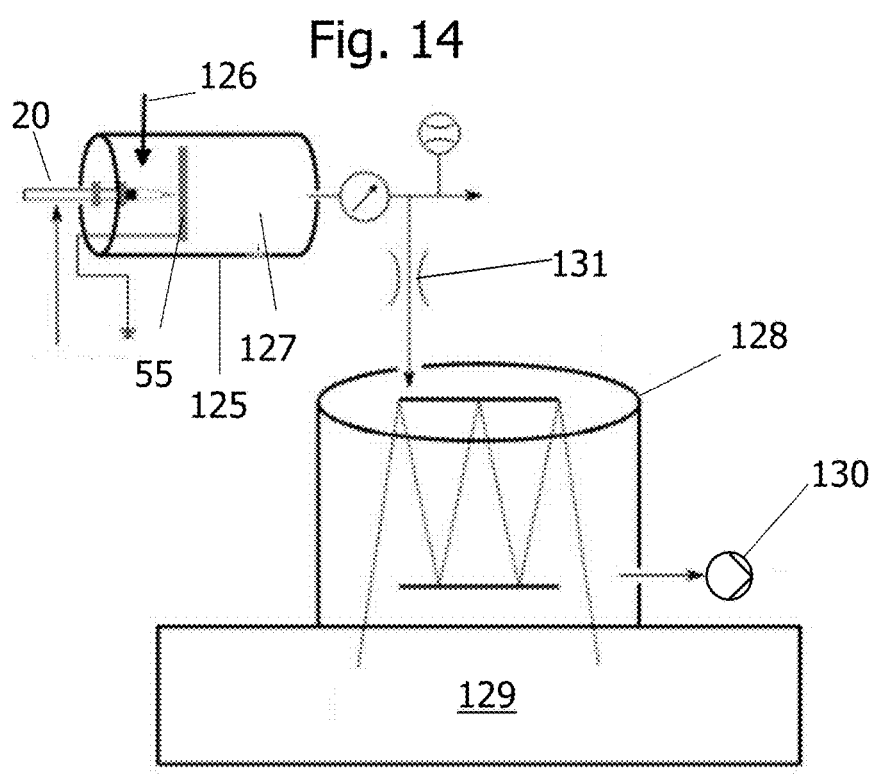

FIG. 14 shows the measurement arrangement for carrying out the FTIR spectroscopy. The gas treated by the therapeutic device 20, which is supplied to a container 125 through a room air inlet 126, is collected in a gas collection cell 127 and drawn into a multi-pass absorption cell (MPC) 128, which is connected to a Bruker Vertex 80v spectrometer 129. The MPC 128 has an optical path length L of 32 m and therefore also allows the measurement of small densities n of absorbing species. A vacuum pump 130 enables the room air to be introduced into the container 125 and into the MPC 128. A pressure of 100 mbar was obtained in the MPC 128 by means of the vacuum pump 130 and inflow throttling by means of a throttle valve 131. The measurements were performed for the highest performing combination (HI) and for the lowest performing combination (LO) of the respective therapeutic device 20. The air flow rate was 30 l/h for all measurements and was measured and checked by an Omega SMA66C flow meter.

A grounded cathode 55 was placed in the container 125 at a distance D=1 mm from the second end 22 of the electrode 1 of the therapeutic device 20.

The measurements cover a wavenumber range from 700 to 4000 cm-1 with a resolution of 0.2 cm$^{-1}$, allowing the detection of species typical of atmospheric cold plasmas, namely $O_3$, NO, $NO_2$, $N_2O$, $N_2O_5$, $HNO_3$, $HNO_2$ and $H_2O_2$. The changes of the concentrations of $CO_2$ and $H_2O$ in the room air were also recorded.

Figure 15:
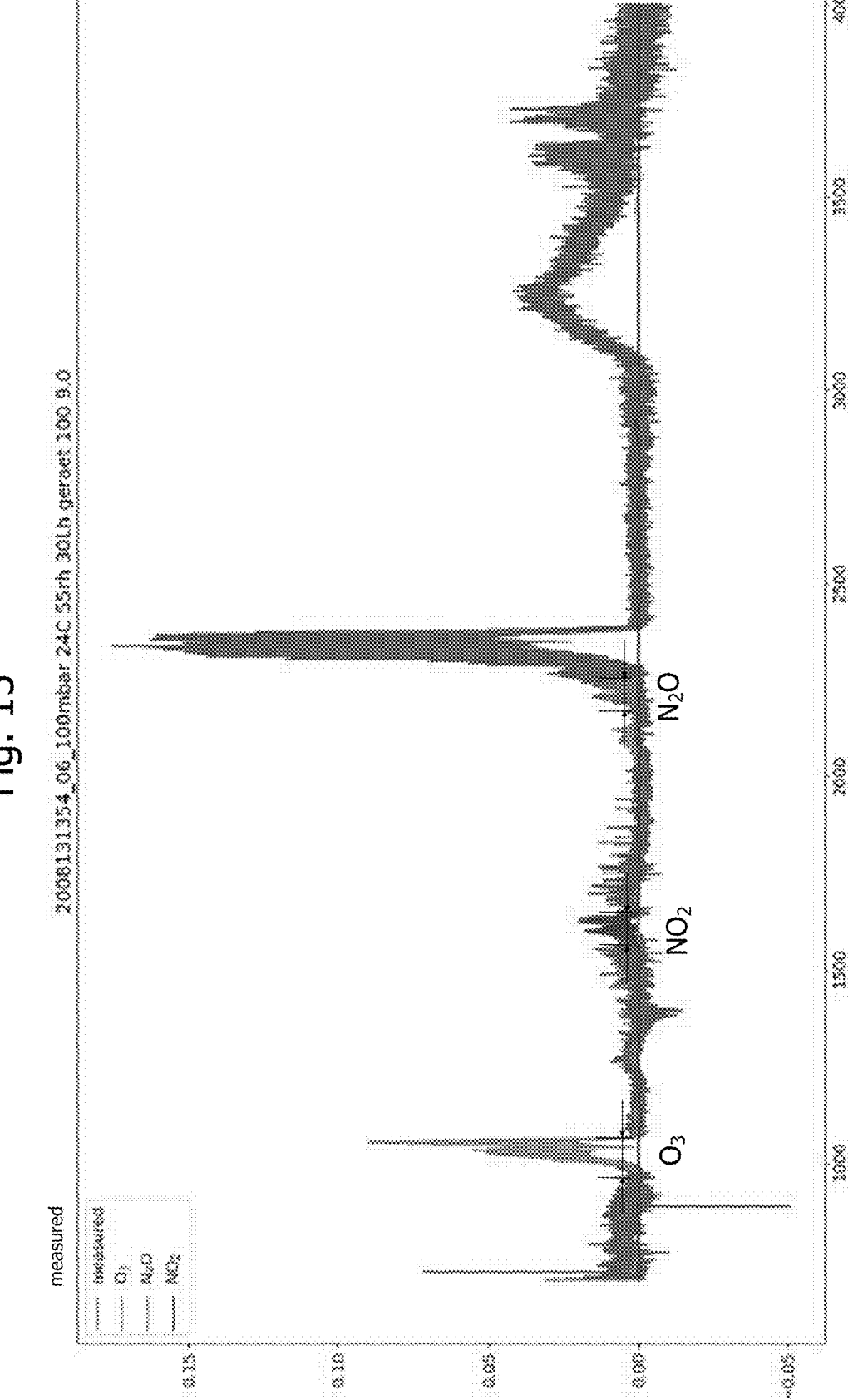

FIG. 15 shows an exemplary spectrum of the first therapeutic device (TV1) with inserted reference spectra for the identified species $O_3$, $N_2O$, $NO_2$. The other absorption peaks relate to $CO_2$ and $H_2O$ or relate to other absorption bands of the identified species. The wave number in $[cm^{-1}]$ is plotted on the abscissa of FIG. 15 and the absorption coefficient A is plotted on the ordinate. The measurement was carried out at 100 mbar at a room temperature of 24° C. and a relative humidity of 55%. The air flow rate amounted to 30 l/h with the most powerful (HI) setting on the therapeutic device.

In particular, the concentration of long-lived oxygen and nitrogen species (RONS) generated by the therapeutic device was measured using FTIR spectroscopy. For medical applications, these species are considered to be one of the key mechanisms to achieve desired treatment effects. Reliable identification and exact quantification of RONS is essential for compliance with DIN SPEC 91315. $O_3$, $N_2O$, $NO_2$ were measured as the species with the highest concentrations. Since the concentrations of $N_2O$ and $NO_2$ were already in the range of 1 ppm, i.e., at the lower end of the measurable range, other species with lower concentrations could no longer be reliably identified. The concentration of $O_3$ was 15 ppm+4 ppm. The concentration of $N_2O$ was 1 ppm+0.05 ppm, the concentration of $NO_2$ was 2 ppm+0.5 ppm. These values were determined for the highest power setting (HI) of the therapeutic device 20. No emissions were detected for the lowest power setting (LO).

Measurement Example 5

Chemical species in the liquid phase were identified for the therapeutic device. For this purpose, a saline solution was prepared in a 24-well titer plate consisting of 500 μl water and 500 μl NaCl saline solution. The second end 22 of the electrode 1 was positioned vertically above the liquid surface at a distance of 1 up to and including 2 mm. Plasma treatment was applied directly to the liquid surface for 10 s, 30 s, 60 s, 180 s, 300 s.

To determine the stability and to compare the production of reactive oxygen species (ROS) from seven electrodes, the enrichment of $H_2O_2$ was determined immediately after contact with the plasma. Chemical parameters were determined immediately after contact with the plasma.

PH values were determined using the HANNA edge blu pH meter (Hanna instruments) based on a glass body electrode in water and NaCl.

Figure 17A:
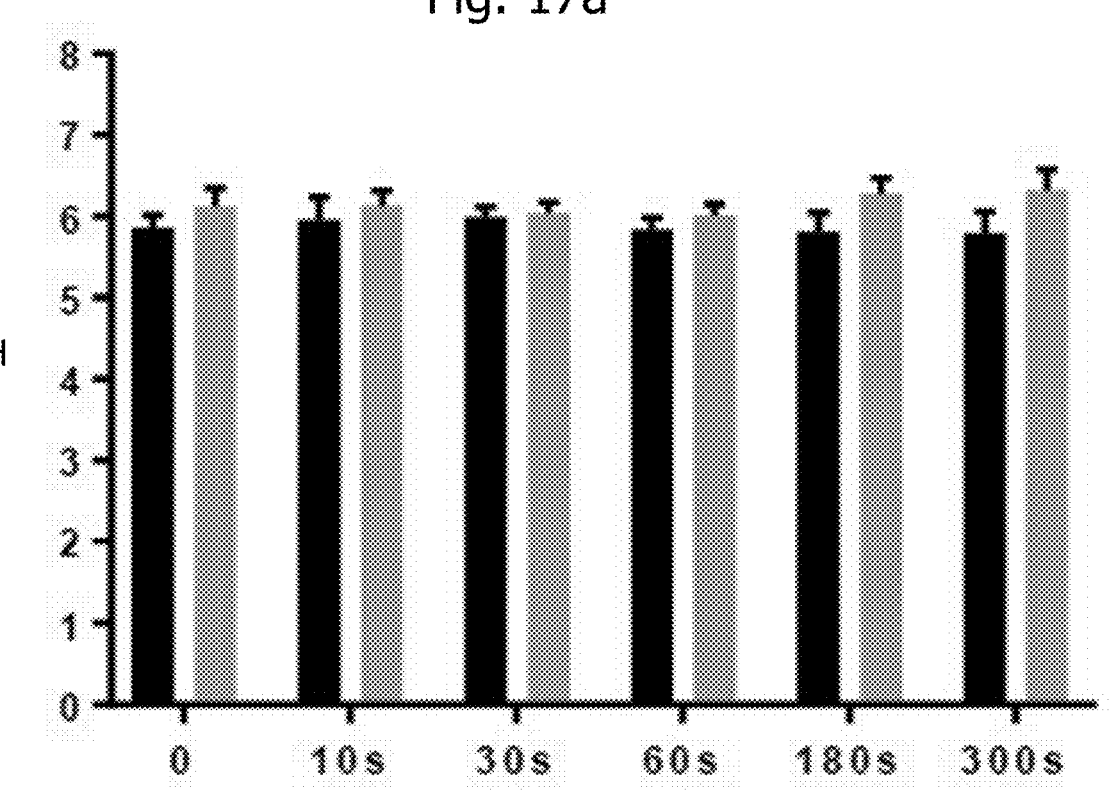

FIG. 17*a* shows the pH value, which is plotted on the ordinate, as a function of the selected measurement duration, which is plotted on the abscissa, for the first therapeutic device (TV1). The measured values were determined here for the treatment duration of 0 s (reference value), 10 s, 30 s, 60 s, 180 s, 300 s for the LO setting of the therapeutic device (TV1). The bar on the left (black) corresponds to the pH value for $H_2O$, the corresponding bar on the right (grey) corresponds to the corresponding value for NaCl. The pH reading remains largely constant for the LO setting for both $H_2O$ and NaCl, i.e., the pH reading does not change with increasing treatment time.

Figure 17B:
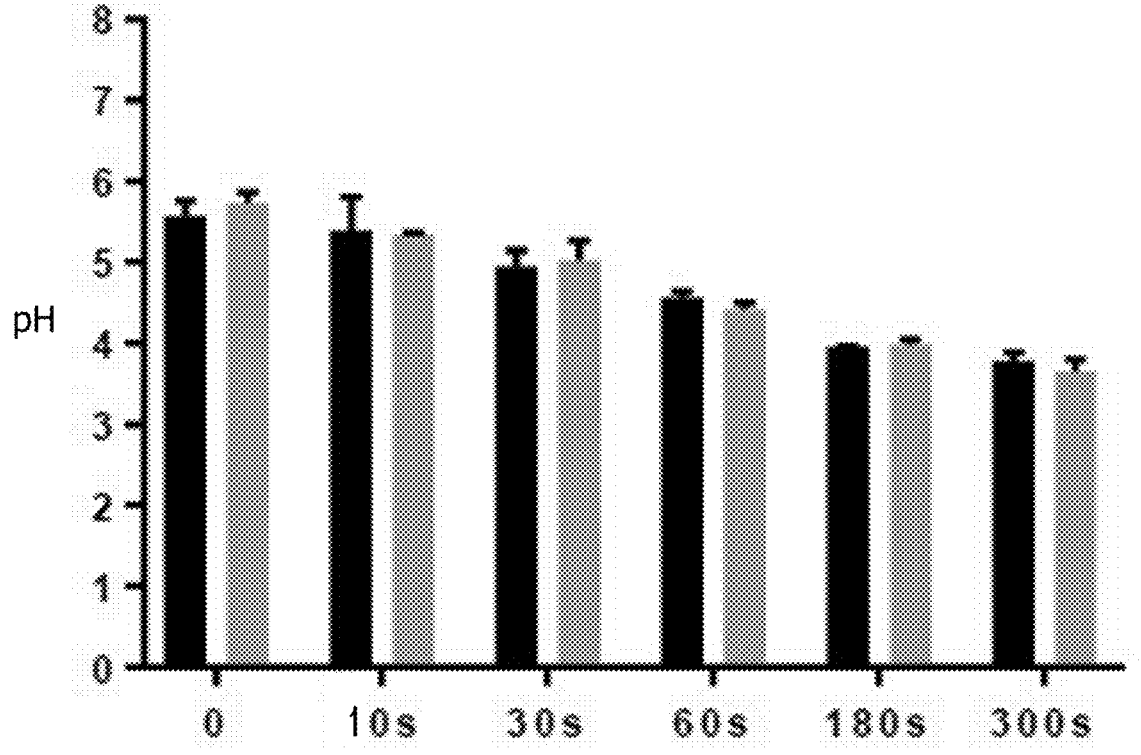

FIG. 17*b* shows the pH value, which is plotted on the ordinate, as a function of the selected measurement duration, which is plotted on the abscissa, for the first therapeutic device (TV1). The measured values were determined for the treatment duration of 0 s (reference value), 10 s, 30 s, 60 s, 180 s, 300 s for the HI setting of the therapeutic device (TV1). The bar on the left (black) corresponds to the pH value for $H_2O$, the corresponding bar on the right (grey) corresponds to the corresponding value for NaCl. The pH value decreases for the HI setting both for $H_2O$ and for NaCl with increasing treatment duration, i.e., acidification increases in both liquids with increasing treatment duration. The acidification in both liquids correlates with the treatment duration, for $H_2O$ the pH value decreased from 5.57 to 3.78, for NaCl the pH value decreased from 5.73 to 3.66.

FIG. 17*c* shows the pH value, which is plotted on the ordinate, as a function of the selected measurement duration, which is plotted on the abscissa, for the therapeutic device (TV2) in water. The measured values were determined for the treatment duration of 0 s (reference value), 10 s, 30 s, 60 s, 180 s, 300 s.

FIG. 17*d* shows the pH value, which is plotted on the ordinate, as a function of the selected measurement duration, which is plotted on the abscissa, for the therapeutic device (TV2) in NaCl. The measured values were determined for the treatment duration of 0 s (reference value), 10 s, 30 s, 60 s, 180 s, 300 s.

The pH value measured for the second therapeutic device (TV2) decreases both for $H_2O$ and for NaCl with increasing treatment duration, i.e., increasing acidification occurs in both liquids with increasing treatment duration. The acidification in both liquids correlates with the treatment duration, for $H_2O$ the pH reading decreased from 5.46 (+/−0.148) to 3.51 (+/−0.03), for NaCl the pH reading decreased from 5.87 (+/−0.3) down to 3.44 (+/−0.04).

FIG. 17*e* shows the pH value, which is plotted on the ordinate, as a function of the selected measurement duration, which is plotted on the abscissa, for the therapeutic device (TV3) with a first electrode in water. The measured values were determined here for the treatment duration of 0 s (reference value), 10 s, 30 s, 60 s, 180 s, 300 s. The pH value in water decreased with increasing treatment time, i.e., acidification occurs. The mean pH dropped from 6.92 to 3.98.

FIG. 17*f* shows the pH value, which is plotted on the ordinate, as a function of the selected measurement duration, which is plotted on the abscissa, for the therapeutic device (TV3) with a second electrode in water. The measured values were determined for the treatment duration of 0 s (reference value), 10 s, 30 s, 60 s, 180 s, 300 s. The pH value in water decreased with increasing treatment time, i.e., acidification occurs. The mean pH dropped from 7.15 to 4.37.

The concentration of $H_2O_2$ was determined for the first and the third therapeutic device (TV1, TV3) by means of a photometric sample using the commercially available Amplex Red reagent (10-acetyl-3,7-dihydroxphenoaxazine, molecular formula $C_{14}H_{11}NO_4$, CAS name/no: 10H-Phenoxazine-3,7-diol, 10-acteyl-119171-73-2, molecular weight 257.25). A color reaction indicates the presence of $H_2O_2$. The absorption was quantified photometrically at a wavelength of 535 nm using an Infinite® M200 PRO Tecan microplate photometer. Measurements were carried out four times (n=4) for the HI and LO settings of the therapeutic device (TV1) except for the comparison of the electrodes for which only one HI setting was used for n=3.

FIG. 18*a* shows the total concentration of $H_2O_2$ in [μM], plotted on the ordinate, as a function of the treatment duration, plotted on the abscissa. The measurements were only documented for the HI settings of the first therapeutic device (TV1), for the LO settings the concentrations of $H_2O_2$ were below the detection threshold and outside the lowest standard point. The bar on the left (black) corresponds to the $H_2O_2$ value for $H_2O$, the corresponding bar on the right (grey) corresponds to the corresponding $H_2O_2$ value for NaCl.

The total concentration increased with increasing treatment duration for both $H_2O$ and NaCl. The concentration of $H_2O_2$ in water was 3 μM after 10 s with a standard deviation of 0.1 ppm and reached 44.35 μM with a standard deviation of 1.51 ppm after 300 s. The concentration of $H_2O_2$ in NaCl was 2.58 μM after 10 s with a standard deviation of 0.08 ppm and reached 42 μM with a standard deviation of 1.43 ppm after 300 s. The concentrations in NaCl appear to be lower than in water, but the deviations remained within the standard deviations.

Figures 18B, 18C, 19, 20, 21, 22A, 22B:
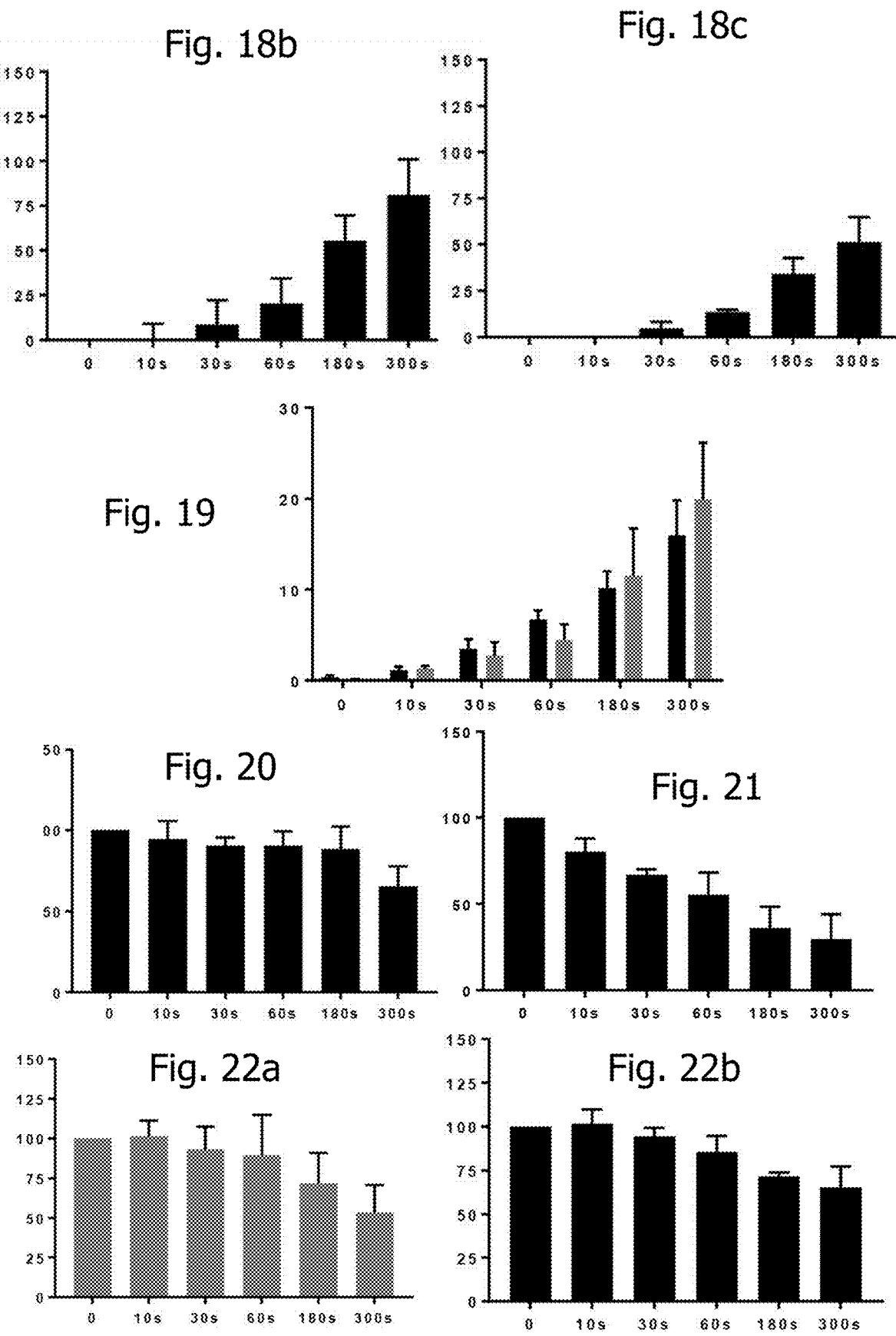

FIG. 18*b* shows the concentration of $H_2O_2$ in [μM], plotted on the ordinate as a function of the treatment duration plotted on the abscissa in water for the second therapeutic device (TV2). For the second therapeutic device, the $H_2O_2$ concentrations were determined using a photometric test series based on titanium (IV) on/sulfate (TiOSO$_4$). TiOSO$_4$ reacts in the presence of $H_2O_2$ to form a yellow-orange complex. The absorption was quantified photometrically at a wavelength of 407 nm using an Infinite® M200 PRO Tecan microplate photometer. The measurements were carried out four times (n=4). The concentrations were determined according to a standard curve for $H_2O_2$ at different dilutions. For very short exposure times (0 s, 10 s), the values were below the detection limit and therefore not included in the calculations and are also not included in table 2.

TABLE 2

| | NaCl | | | $H_2O$ | | |
|---|---|---|---|---|---|---|
| t | MW | SD | n | MW | SD | n |
| 30 s | 4.86 | 3.28 | 3 | 19.56 | 8.31 | 2 |
| 60 s | 13.56 | 1.19 | 2 | 20.28 | 13.98 | 4 |
| 180 s | 33.89 | 8.61 | 4 | 55.27 | 14.13 | 4 |
| 300 s | 51.17 | 13.47 | 4 | 81.04 | 19.89 | 4 |

The concentrations increased with increasing treatment duration in water, as well as in NaCl. After a short treatment duration of 10 s or 30 s, the concentration of $H_2O_2$ is within the detection limit of the experimental device (<5 μM). The standard deviations are therefore higher for a treatment duration >60 s. The maximum concentration was higher in water (81.04 μM) than in NaCl (51.17) at a treatment duration of 300 s.

FIG. 18*c* shows the concentration of $H_2O_2$ in [μM], plotted on the ordinate, as a function of the treatment duration, plotted on the abscissa, in NaCl for the second therapeutic device (TV2).

The concentration of $H_2O_2$ in [μM] is plotted on the ordinate, as a function of the treatment duration, plotted on the abscissa, in water for the first electrode of the third therapeutic device (TV3) and the concentration of $H_2O_2$ for the second electrode of the third therapeutic device. Both electrodes were enriched with $H_2O_2$ depending on the treatment duration, whereby a concentration of 30 μM (1.015 ppm) was reached for the first electrode and a concentration of 18.34 μM (0.624 ppm) was reached for the second electrode after 300 s of treatment duration.

A colorimetric reagent was used to determine nitrites and nitrates (Griess assay; Cayment chemicals), the determination being carried out using a microtiter plate. In order to measure the total nitrate/nitrite concentration, in a first step nitrate is converted to nitrite using nitrate reductase and in a second step the nitrite is converted into a dark purple azo compound with the addition of the Griess reagent, wherein the nitrite was determined without a conversion of the nitrate reductase. Standard curves for both compounds were included in the test procedure. A photometric measurement of the absorption coefficient at a wavelength of 540 nm using the Infinite® M200 PRO Tecan microplate photometer determines the exact concentrations of nitrite and nitrate. The measurements were repeated twice with n=3 for the first therapeutic device (TV1) and twice with n=5 for the second therapeutic device (TV2).

FIG. 19 shows the total concentration of $NO_2^-$ and/or $NO_3^-$ in [μM] plotted on the ordinate versus the treatment duration plotted on the abscissa for the first therapeutic device (TV1). The measurements were only documented for the HI settings of the therapeutic device 20; for the LO settings the concentrations of $NO_2^-$ and $NO_3^-$ were below the detection threshold and outside the lowest standard point. In FIG. 19*a*, the left-hand bar (grey) corresponds to the $NO_2^-$ measured value in $H_2O$, the corresponding right-hand bar (black) corresponds to the $NO_3^-$ measured value in $H_2O$. The total concentration increased with increasing treatment duration for both $NO_2^-$ and $NO_3^-$. Thus, the concentration curves for the HI settings show an increase in both the nitrate concentration ($NO_3^-$) and the nitrite concentration ($NO_2^-$) in water, which depends on the treatment duration. The proportion of nitrite is lower than the proportion of nitrate in water.

In FIG. 19, the left-hand bar (black) corresponds to the $NO_2^-$ measured value in $H_2O$, the corresponding right-hand bar (grey) corresponds to the $NO_2^-$ measured value in NaCl. The total concentration increased with increasing treatment duration for both $NO_2^-$ in water and $NO_2^-$ in NaCl. Thus, the concentration curves for the HI settings show an increase in the nitrite concentration ($NO_2^-$) both in water and in NaCl that is dependent on the treatment duration. The concentration of nitrite appears to be lower in water than in NaCl.

Measurement Example 6

The cytotoxicity was determined by means of an MTT test (MTT assay) using the adherent skin fibroblast cell line GM00637, as described in DIN SPEC 91315. A yellow, water-soluble 3-(4,5-dimethylthiazol-2-yl)-2,5-diphenyltet-razolium bromide (MTT) is converted to a blue-purple formazan and the photometric absorption coefficient is monitored for drawing conclusions on cell viability. The absorption coefficient was recorded using an Infinite® M200 PRO Tecan microplate photometer at 550 nm.

The cells were obtained from the Coriell Institute (Camden, New Jersey, USA) and stored in DMEM High Glucose w/L Glutamine (Corning®) medium containing 10% fetal bovine serum (FBS; Biochrome AG, Berlin, Germany) and 1% penicillin/streptomycin (Corning®) were added. The culture was stored at a temperature of 37° C. and 5% $CO_2$.

On the day before the treatment, $0.5 \times 10^5$ cells per microtiter plate were applied to a 24-well titer plate and inoculated as previously described. The number of cells and the volumes used were adapted to the 24-well titer plate in accordance with DIN SPEC 91315, corresponding to the size of the plasma source of the therapeutic device.

Before plasma treatment, the cell culture medium was removed, the cells were washed twice with phosphate buffered saline (pH=7.4) and covered with 150 μl of PBS. The cells were exposed to the plasma source for 10 s, 30 s, 60 s, 180 s, 300 s (in triplicate measurements). Untreated cells served as a reference. Immediately after the spot plasma treatments, i.e., a maximum of 5 min after the plasma treatment, 450 µl of fresh DMEM with 13% FBS were added per well (indentation). The cell culture plates were incubated for a period of 48 hours. Subsequently, the supernatant medium was replaced with fresh DMEM with 10% FCS containing 15 µl MTT solution (5 mg/ml in PBS).

After 2 h, the MTT medium solution was removed and the cells were washed twice with PBS, after which 300 ml of cell lysis solution (DMSO/neat acetic acid/SDS) was added. Finally, the absorption coefficient was monitored, and the cytotoxicity was determined relative to an untreated reference corresponding to 100%. An IC-50 time was calculated, which corresponds to 50% cell viability.

FIG. 20 shows the results of the MTT test for the first therapeutic device (TV1), the treatment duration being plotted on the abscissa and the cytotoxicity in % being plotted on the ordinate. The plasma treatment was well tolerated by the cells. After an exposure period of 300 s, cell viability was still 65.5%, i.e., the IC-50 time for the therapeutic device is above 300 s. For all other treatment durations, viability was approximately 90% with a marginal decrease with increasing treatment time.

FIG. 21 shows the results of the MTT test for the second therapeutic device (TV2). The room temperature was 22.1 degrees Celsius, and the average relative humidity was 56.6% (range from 51 up to and including 60.3%). The treatment duration is plotted on the abscissa and the cytotoxicity in % is plotted on the ordinate. Cell viability decreased with increasing treatment duration, consistent with an increase in cytotoxicity with increased plasma exposure duration. The calculated IC-50 time for the second therapeutic device was 65.14 s. After the longest treatment duration of 300 s, on average only 26.5% of the cells were still vital. The standard deviations for the treatment durations of 60 s, 180 s and 300 s were relatively high at >10%.

Table 3 shows the measurements forming the basis for FIG. 21:

TABLE 3

| time | Test 1 | Test 2 | Test 3 | MW | SD |
|---|---|---|---|---|---|
| 10 s | 71.37 | 84.53 | 84.76 | 80.217 | 7.663 |
| 30 s | 64.42 | 66.02 | 70.49 | 66.977 | 3.145 |
| 60 s | 40.98 | 58.60 | 66.19 | 55.254 | 12.935 |
| 180 s | 22.51 | 39.52 | 46.45 | 36.16 | 12.318 |
| 300 s | 19.04 | 46.00 | 23.97 | 29.67 | 14.357 |

The results of the MTT tests for the first and second electrode of the third therapeutic device (TV3) are shown in FIGS. 22a and 22b. The treatment duration is plotted on the abscissa and the cytotoxicity in % is plotted on the ordinate. After the longest treatment duration, cell viability decreased to 53.59% (+17.22%) for the first electrode and 65.28% (+12.05%) for the second electrode. The IC-50 time was greater than 300 s for both electrodes.

Measurement Example 7

An inhibition zone assay was used to determine the antimicrobial effectiveness of the plasma source in the form of the LSE electrode in accordance with DIN SPEC 91315:2014-06. The bacterium *Staphylococcus aureus* DSM 799/ATCC 6538 and the bacterium *Staphylococcus epidermidis* DSM 20044/ATCC 14990 (DSM German Collection of Microorganisms and Cell Cultures; ATCC American Type Culture Collection) were used for the measurement. The bacterium *Escherichia coli* K-12 DSM 11250/NCTC 10538 (NCTC National Collection of Type Cultures) was used for a further measurement. The bacterium *Pseudomonas aeruginosa* DSM 50071/ATCC 10145 was used for a further measurement. The yeast *Candida albicans* DSM 1386/ATCC 10321 was used for a further measurement.

For the tests with the LSE electrode, 100 µl of a solution of the bacterium *Staphylococcus aureus* (number of cells approximately $10^6$/ml–colony forming units/a) was distributed on a moist solid medium (soybean casein digestion agar Carl Roth GmbH & Co. KG, Karlsruhe, Germany) and selectively treated with the plasma source, the LSE electrode. The treatment time was 1, 2, 3, 4 or 5 min, with the growth inhibition zone test being carried out on the moist agar surface (N=6). The distance between the plasma source and the surface of the wet solid was approximately 1.5 mm. A cathode was positioned under the agar plates.

After incubation of the agar plates with a diameter of 84 mm at a temperature of 37° C., the dimensions of the growth inhibition zones were measured in mm, wherein the growth inhibition zones are defined as the area with no visible growth of microorganisms. If the growth inhibition zone was not circular, the mean diameter was determined from measurements of the largest and smallest diameters. For comparison, agar plates were seeded but not subjected to plasma treatment. They are shown in FIG. 23 at the times t=0 min to t=5 min.

TABLE 4a

| | 1 min | | DM [mm] | 2 min | | DM [mm] |
|---|---|---|---|---|---|---|
| 1 | 35.00 | 40.00 | 37.50 | 40.00 | 45.00 | 42.50 |
| 2 | 41.00 | 42.00 | 41.50 | 42.00 | 43.00 | 42.50 |
| 3 | 38.00 | 41.00 | 39.50 | 41.00 | 42.00 | 41.50 |
| 4 | 40.00 | 42.00 | 41.00 | 39.00 | 40.00 | 39.50 |
| 5 | 40.00 | 41.00 | 40.50 | 36.00 | 38.00 | 37.00 |
| 6 | 39.00 | 40.00 | 39.50 | 40.00 | 41.00 | 40.50 |
| MW | | | 39.92 | | | 40.58 |
| SD | | | 1.43 | | | 2.11 |

TABLE 4b

| | 3 min | | DM [mm] | 4 min | | DM [mm] |
|---|---|---|---|---|---|---|
| 1 | 44.00 | 45.00 | 44.50 | 42.00 | 45.00 | 43.50 |
| 2 | 42.00 | 44.00 | 43.00 | 45.00 | 45.00 | 45.00 |
| 3 | 43.00 | 45.00 | 44.00 | 45.00 | 46.00 | 45.50 |
| 4 | 44.00 | 45.00 | 44.50 | 44.00 | 45.00 | 44.50 |
| 5 | 45.00 | 48.00 | 46.50 | 43.00 | 45.00 | 44.00 |
| 6 | 45.00 | 45.00 | 45.00 | 45.00 | 45.00 | 45.00 |
| MW | | | 44.58 | | | 44.58 |
| SD | | | 1.16 | | | 0.74 |

TABLE 4c

| | 5 min | | DM [mm] |
|---|---|---|---|
| 1 | 42.00 | 45.00 | 43.50 |
| 2 | 45.00 | 45.00 | 45.00 |
| 3 | 43.00 | 44.00 | 43.50 |
| 4 | 43.00 | 43.00 | 43.00 |
| 5 | 45.00 | 44.00 | 44.50 |
| 6 | 45.00 | 46.00 | 45.50 |
| MW | | | 44.17 |
| SD | | | 0.98 |

The treatment of the described agar plates, inoculated with bacteria as previously indicated, with the plasma source of the LSE electrode of the therapeutic device thus resulted in growth inhibition zones for *Staphylococcus aureus*. The size of the zones depended on the treatment duration. In each case, 6 agar plates were treated with the plasma source for 1 min, 2 min, 3 min, 4 min, 5 min. An exemplary example is shown in FIG. 23.

FIG. 24 is a graphical representation of the mean values (MV) according to table 4a to table 4c and the associated standard deviations (SD) in a bar chart in which the treatment durations are plotted on the abscissa and the mean diameters in mm are plotted on the ordinate.

The size of the growth inhibition zone increased only partially with increasing treatment duration. Therefore, the influence of the treatment duration on the size of the growth inhibition zone was less pronounced than for the formation of ROS, see in particular FIG. 22. The antimicrobial area was slightly larger than the corresponding area created by the ROS formation, so that additional antimicrobial effects can be assumed. However, the number of remaining colonies within the growth inhibition zone steadily decreased with increasing treatment duration.

In comparison, the measurements with EWC electrodes showed growth inhibition zones with diameters of 14 mm for a treatment duration of 1 min up to and including 16 mm for a treatment duration of 5 min for *Staphylococcus aureus*.

For the tests of the first therapeutic device (TV1), 100 µl of the corresponding microorganism solution (number of cells approximately $10^6$/ml–colony forming units/a) was distributed on a moist solid medium (soybean casein digestion agar Carl Roth GmbH & Co. KG, Karlsruhe, Germany) and selectively treated with the plasma source, the EWC electrode. The treatment time was 1, 2, 3, 4 or 5 min, with the growth inhibition zone test being carried out on the moist agar surface (N=6). The distance between the plasma source and the surface of the wet solid was approximately 1.5 mm. A cathode was positioned under the agar plates.

After incubation of the agar plates with a diameter of 84 mm at a temperature of 37° C., the dimensions of the growth inhibition zones were measured in mm, wherein the growth inhibition zones are defined as the area with no visible growth of microorganisms. If the growth inhibition zone was not circular, the mean diameter was determined from measurements of the largest and smallest diameters.

For comparison, agar plates were seeded but not subjected to plasma treatment. They are shown in FIG. 25 at the times t=0 min to t=5 min.

Figure 26:
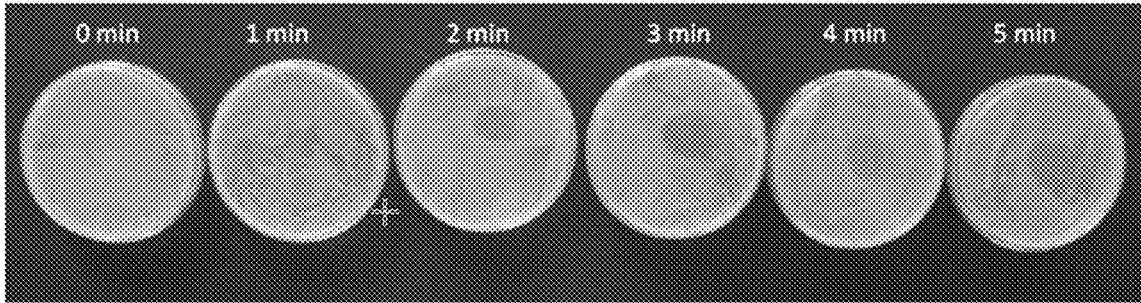

For the bacterium *Staphylococcus epidermidis* they are shown in FIG. 26 at times t=0 min to t=5 min.

Figure 27:
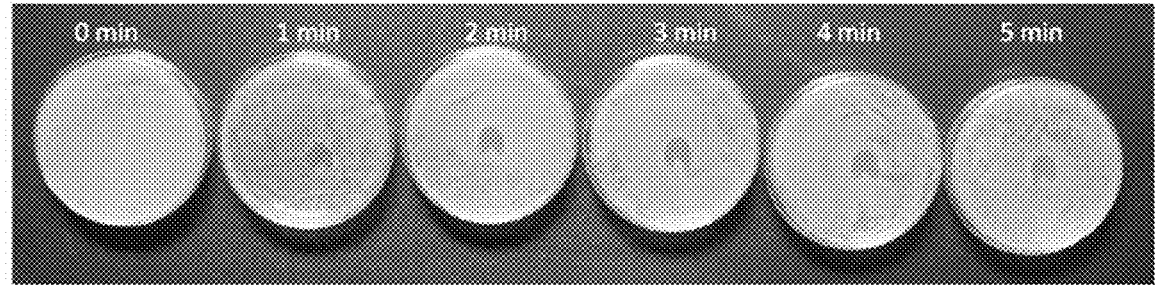

For the bacterium *Escherichia coli*, they are shown in FIG. 27 at times t=0 min to t=5 min.

Figure 28:
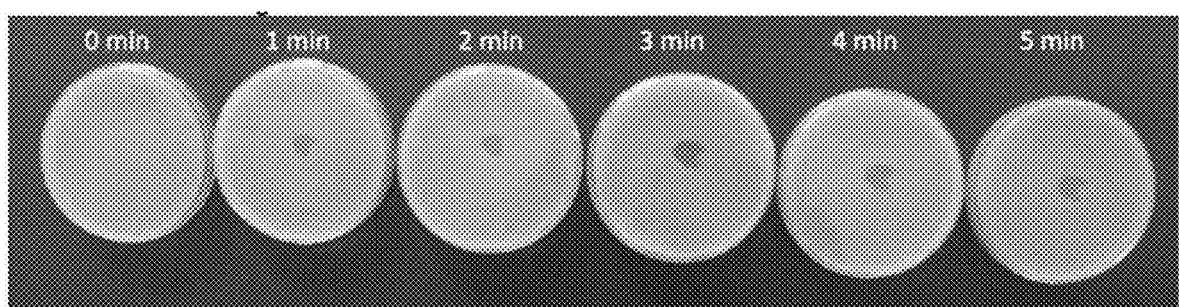

For the bacterium *Pseudomonas aeruginosa* they are shown in FIG. 28 at times t=0 min to t=5 min.

Figure 29:
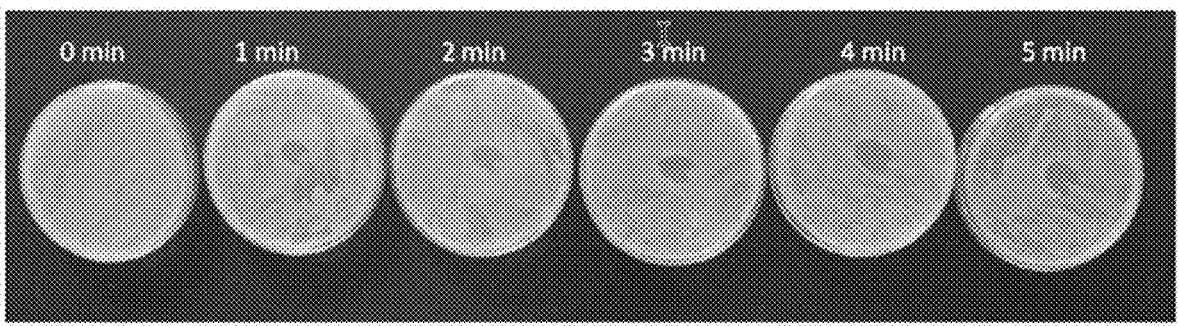

For the yeast *Candida albicans* they are shown in FIG. 29 at times t=0 min to t=5 min.

Table 5a, 5b, 5c below shows the measured values for the bacterium *Staphylococcus aureus* at times t=0 min to t=5 min at 25.4° C. and a relative humidity of 46%.

TABLE 5a

|   | 1 min | | DM [mm] | 2 min | | DM [mm] |
|---|---|---|---|---|---|---|
| 1 | 14.50 | 13.00 | 13.75 | 16.50 | 14.00 | 15.25 |
| 2 | 16.00 | 14.00 | 15.00 | 17.00 | 15.00 | 16.00 |
| 3 | 16.50 | 15.00 | 15.75 | 16.50 | 14.00 | 15.25 |
| 4 | 15.50 | 15.00 | 15.25 | 17.50 | 13.00 | 15.25 |
| 5 | 17.00 | 15.00 | 16.00 | 19.50 | 19.00 | 19.25 |

TABLE 5a-continued

|   | 1 min | | DM [mm] | 2 min | | DM [mm] |
|---|---|---|---|---|---|---|
| 6 | 15.50 | 14.00 | 14.75 | 17.50 | 16.00 | 16.75 |
| MW | | | 15.08 | | | 16.29 |
| SD | | | 0.80 | | | 1.57 |

TABLE 5b

|   | 3 min | | DM [mm] | 4 min | | DM [mm] |
|---|---|---|---|---|---|---|
| 1 | 18.50 | 16.00 | 17.25 | 20.00 | 16.00 | 18.00 |
| 2 | 18.00 | 14.00 | 16.00 | 19.50 | 17.00 | 18.25 |
| 3 | 19.00 | 15.00 | 17.00 | 18.50 | 16.00 | 17.25 |
| 4 | 18.50 | 16.00 | 17.25 | 21.50 | 17.00 | 19.25 |
| 5 | 19.50 | 16.00 | 17.75 | 20.50 | 18.00 | 19.25 |
| 6 | 19.50 | 16.00 | 17.75 | 19.00 | 16.00 | 17.50 |
| MW | | | 17.17 | | | 18.25 |
| SD | | | 0.65 | | | 0.85 |

TABLE 5c

|   | 5 min | | DM [mm] |
|---|---|---|---|
| 1 | 19.00 | 16.00 | 17.50 |
| 2 | 20.00 | 16.00 | 18.00 |
| 3 | 19.50 | 16.00 | 17.75 |
| 4 | 19.00 | 17.00 | 18.00 |
| 5 | 20.50 | 17.00 | 18.75 |
| 6 | 22.00 | 18.00 | 20.00 |
| MW | | | 18.33 |
| SD | | | 0.92 |

Table 6a, 6b, 6c below shows the measured values for the *Staphylococcus epidermidis* bacterium at times t=0 min to t=5 min at 25.6° C. and a relative humidity of 44%.

TABLE 6a

|   | 1 min | | DM [mm] | 2 min | | DM [mm] |
|---|---|---|---|---|---|---|
| 1 | 19.00 | 17.00 | 18.00 | 24.00 | 23.00 | 23.50 |
| 2 | 17.00 | 15.00 | 16.00 | 20.00 | 16.00 | 18.00 |
| 3 | 18.00 | 15.00 | 16.50 | 21.50 | 19.00 | 20.25 |
| 4 | 17.00 | 12.00 | 14.50 | 22.00 | 19.00 | 20.50 |
| 5 | 17.00 | 13.00 | 15.00 | 20.00 | 20.00 | 20.00 |
| 6 | 18.00 | 13.00 | 15.50 | 21.00 | 17.00 | 19.00 |
| MW | | | 15.92 | | | 20.21 |
| SD | | | 1.24 | | | 1.86 |

TABLE 6b

|   | 3 min | | DM [mm] | 4 min | | DM [mm] |
|---|---|---|---|---|---|---|
| 1 | 21.00 | 19.00 | 20.00 | 26.00 | 23.00 | 24.50 |
| 2 | 28.50 | 23.00 | 25.75 | 29.50 | 30.00 | 29.75 |
| 3 | 27.50 | 23.00 | 25.25 | 25.00 | 25.00 | 25.00 |
| 4 | 20.50 | 17.00 | 18.75 | 29.00 | 29.00 | 29.00 |
| 5 | 24.00 | 21.00 | 22.50 | 26.00 | 25.00 | 25.50 |
| 6 | 22.50 | 20.00 | 21.25 | 23.00 | 20.00 | 21.50 |
| MW | | | 22.25 | | | 25.88 |
| SD | | | 2.82 | | | 3.06 |

TABLE 6c

|   | 5 min | | DM [mm] |
|---|---|---|---|
| 1 | 23.00 | 23.00 | 23.00 |
| 2 | 23.00 | 19.00 | 21.00 |
| 3 | 25.00 | 25.00 | 25.00 |

TABLE 6c-continued

|  | 5 min |  | DM [mm] |
| --- | --- | --- | --- |
| 4 | 25.00 | 23.00 | 24.00 |
| 5 | 27.00 | 25.00 | 26.00 |
| 6 | 23.50 | 20.00 | 21.75 |
| MW |  |  | 23.46 |
| SD |  |  | 1.91 |

Table 7a, 7b, 7c below shows the measured values for the bacterium *Escherichia coli* at times t=0 min to t=5 min at 24.5° C. and a relative humidity of 49%.

TABLE 7a

|  | 1 min |  | DM [mm] | 2 min |  | DM [mm] |
| --- | --- | --- | --- | --- | --- | --- |
| 1 | 16.50 | 10.00 | 13.25 | 15.50 | 11.00 | 13.25 |
| 2 | 14.00 | 11.00 | 12.50 | 16.00 | 12.00 | 14.00 |
| 3 | 14.50 | 11.00 | 12.75 | 15.00 | 12.00 | 13.50 |
| 4 | 15.00 | 11.00 | 13.00 | 16.50 | 13.00 | 14.75 |
| 5 | 13.50 | 9.00 | 11.25 | 15.00 | 11.00 | 13.00 |
| 6 | 15.00 | 10.00 | 12.50 | 16.00 | 13.00 | 14.50 |
| MW |  |  | 15.92 |  |  | 20.21 |
| SD |  |  | 1.24 |  |  | 1.86 |

TABLE 7b

|  | 3 min |  | DM [mm] | 4 min |  | DM [mm] |
| --- | --- | --- | --- | --- | --- | --- |
| 1 | 16.50 | 14.00 | 15.25 | 16.50 | 13.00 | 14.75 |
| 2 | 17.00 | 15.00 | 16.00 | 17.00 | 13.00 | 15.00 |
| 3 | 16.00 | 11.00 | 13.50 | 16.50 | 14.00 | 15.25 |
| 4 | 16.50 | 13.00 | 14.75 | 18.50 | 16.00 | 17.25 |
| 5 | 16.50 | 14.00 | 15.25 | 17.00 | 13.00 | 15.00 |
| 6 | 17.00 | 14.00 | 15.50 | 17.00 | 14.00 | 15.50 |
| MW |  |  | 22.25 |  |  | 25.88 |
| SD |  |  | 2.82 |  |  | 3.06 |

TABLE 7c

|  | 5 min |  | DM [mm] |
| --- | --- | --- | --- |
| 1 | 15.50 | 11.00 | 13.25 |
| 2 | 18.50 | 14.00 | 16.25 |
| 3 | 16.50 | 12.00 | 14.25 |
| 4 | 16.50 | 13.00 | 14.75 |
| 5 | 16.00 | 12.00 | 14.00 |
| 6 | 17.00 | 16.00 | 16.50 |
| MW |  |  | 23.46 |
| SD |  |  | 1.91 |

Table 8a, 8b, 8c below shows the measured values for the bacterium *Pseudomonas aeruginosa* at times t=0 min to t=5 min at 25.6° C. and a relative humidity of 44%.

TABLE 8a

|  | 1 min |  | DM [mm] | 2 min |  | DM [mm] |
| --- | --- | --- | --- | --- | --- | --- |
| 1 | 10.00 | 9.00 | 9.50 | 10.00 | 9.00 | 9.50 |
| 2 | 11.50 | 10.00 | 10.75 | 11.50 | 10.00 | 10.75 |
| 3 | 11.00 | 10.00 | 10.50 | 11.00 | 10.00 | 10.50 |
| 4 | 11.00 | 9.00 | 10.00 | 11.00 | 9.00 | 10.00 |
| 5 | 10.00 | 9.00 | 9.50 | 10.00 | 9.00 | 9.50 |
| 6 | 10.00 | 9.00 | 9.50 | 10.00 | 9.00 | 9.50 |
| MW |  |  | 9.96 |  |  | 9.96 |
| SD |  |  | 0.56 |  |  | 0.56 |

TABLE 8b

|  | 3 min |  | DM [mm] | 4 min |  | DM [mm] |
| --- | --- | --- | --- | --- | --- | --- |
| 1 | 15.00 | 11.00 | 13.00 | 14.00 | 11.00 | 12.50 |
| 2 | 14.50 | 11.00 | 12.75 | 14.50 | 11.00 | 12.75 |
| 3 | 14.00 | 11.00 | 12.50 | 14.50 | 12.00 | 13.25 |
| 4 | 15.00 | 11.00 | 13.00 | 12.00 | 11.00 | 11.50 |
| 5 | 14.00 | 11.00 | 12.50 | 12.00 | 10.00 | 11.00 |
| 6 | 14.00 | 10.00 | 12.00 | 13.00 | 12.00 | 12.50 |
| MW |  |  | 12.63 |  |  | 12.25 |
| SD |  |  | 0.38 |  |  | 0.84 |

TABLE 8c

|  | 5 min |  | DM [mm] |
| --- | --- | --- | --- |
| 1 | 12.00 | 9.00 | 10.50 |
| 2 | 13.00 | 10.00 | 11.50 |
| 3 | 13.00 | 10.00 | 11.50 |
| 4 | 14.00 | 11.00 | 12.50 |
| 5 | 13.00 | 10.00 | 11.50 |
| 6 | 14.00 | 11.00 | 12.50 |
| MW |  |  | 11.67 |
| SD |  |  | 0.75 |

Table 9a, 9b, 9c below shows the measured values for the microorganism *Candida albicans* at times t=0 min to t=5 min at 25.1° C. and a relative humidity of 47%.

TABLE 9a

|  | 1 min |  | DM [mm] | 2 min |  | DM [mm] |
| --- | --- | --- | --- | --- | --- | --- |
| 1 | 11.50 | 9.00 | 10.25 | 14.50 | 11.00 | 12.75 |
| 2 | 13.00 | 10.00 | 11.50 | 16.00 | 13.00 | 14.50 |
| 3 | 12.50 | 10.00 | 11.25 | 15.00 | 12.00 | 13.50 |
| 4 | 11.00 | 9.00 | 10.00 | 16.00 | 14.00 | 15.00 |
| 5 | 12.00 | 10.00 | 11.00 | 15.00 | 12.00 | 13.50 |
| 6 | 12.00 | 10.00 | 11.00 | 15.50 | 11.00 | 13.25 |
| MW |  |  | 10.83 |  |  | 13.75 |
| SD |  |  | 0.58 |  |  | 0.84 |

TABLE 9b

|  | 3 min |  | DM [mm] | 4 min |  | DM [mm] |
| --- | --- | --- | --- | --- | --- | --- |
| 1 | 17.50 | 14.00 | 15.75 | 17.00 | 12.00 | 14.50 |
| 2 | 17.00 | 14.00 | 15.50 | 20.00 | 17.00 | 18.50 |
| 3 | 18.00 | 14.00 | 16.00 | 17.00 | 14.00 | 15.50 |
| 4 | 17.00 | 13.00 | 15.00 | 20.00 | 15.00 | 17.50 |
| 5 | 16.50 | 11.00 | 13.75 | 19.00 | 14.00 | 16.50 |
| 6 | 16.00 | 13.00 | 14.50 | 17.00 | 12.00 | 14.50 |
| MW |  |  | 15.08 |  |  | 16.17 |
| SD |  |  | 0.85 |  |  | 1.63 |

TABLE 9c

|  | 5 min |  | DM [mm] |
| --- | --- | --- | --- |
| 1 | 16.00 | 12.00 | 14.00 |
| 2 | 16.00 | 12.00 | 14.00 |
| 3 | 16.00 | 13.00 | 14.50 |
| 4 | 18.50 | 14.00 | 16.25 |
| 5 | 17.00 | 12.00 | 14.50 |
| 6 | 19.00 | 14.00 | 16.50 |
| MW |  |  | 14.96 |
| SD |  |  | 1.12 |

The gram-positive bacteria *Staphylococcus aureus* (15.08-18.33 mm) and *Staphylococcus epidermidis* (15.92-25.88 mm) showed the largest inhibition zone diameters, while the gram-negative strains *Escherichia coli* (12.54-15.46 mm) and *Pseudomonas aeruginosa* (9.96-12.63 mm) and the yeast *Candida albicans* (10.83-16.17 mm) were less affected by plasma treatment with the EWC electrode.

FIG. 30 shows a comparison of the diameter values for the bacteria *Staphylococcus aureus* (bar B1), *Staphylococcus epidermidis* (bar B2), *Escherichia coli* (bar B3), *Pseudomonas aeruginosa* (bar B4) and the yeast *Candida albicans* (bar B5). The treatment duration in minutes was plotted on the abscissa and the inhibition zone diameter in mm on the ordinate. For each series of tests, a decrease in antimicrobial efficacy was noted in the following order:

Staphylococcus epidermidis>Staphylococcus aureus>Escherichia coli=Candida albicans>Pseudomonas aeruginosa.

The size of the growth inhibition zone increased in some cases with increasing treatment duration.

As for the first therapeutic device (TV1), growth inhibition zone tests were also carried out for the second therapeutic device (TV2) for the same microorganisms.

For the bacterium *Staphylococcus aureus*, they are shown in FIG. 31 at times t=0 min to t=5 min.

For the bacterium *Staphylococcus epidermidis* they are shown in FIG. 32 at times t=0 min to t=5 min.

Figure 33:
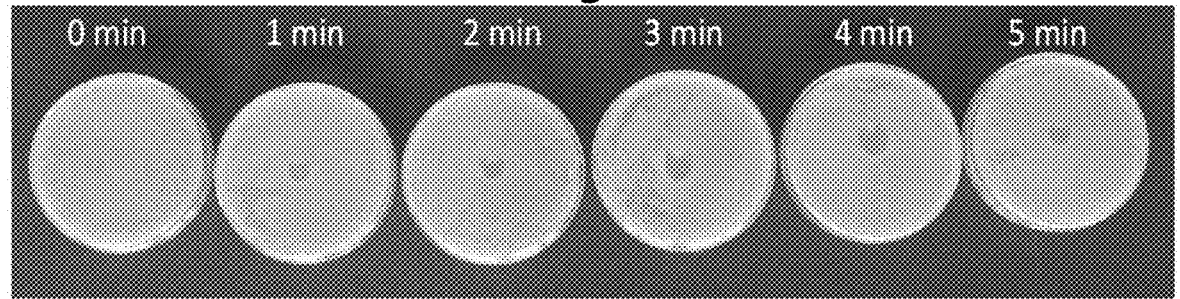
FIG. 33 an illustration of the agar plates for an inhibition zone test for the EWC electrode of the second therapeutic device for the bacterium *Escherichia coli,*

For the bacterium *Escherichia coli*, they are shown in FIG. 33 at times t=0 min to t=5 min.

Figure 34:
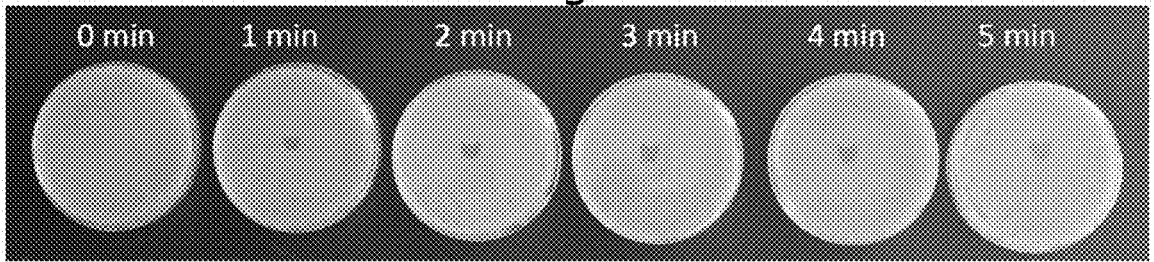
FIG. 34 an illustration of the agar plates for an inhibition zone test for the EWC electrode of the second therapeutic device for the bacterium *Pseudomonas aeruginosa,*

For the bacterium *Pseudomonas aeruginosa* they are shown in FIG. 34 at times t=0 min to t=5 min.

Figure 35:
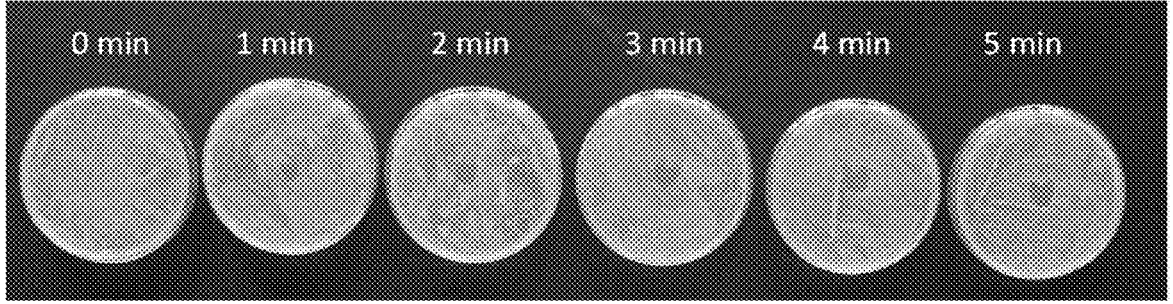
FIG. 35 an illustration of the agar plates for an inhibition zone test for the EWC electrode of the second therapeutic device for the yeast *Candida albicans,*

For the yeast *Candida albicans* they are shown in FIG. 35 at times t=0 min to t=5 min.

Figure 36:
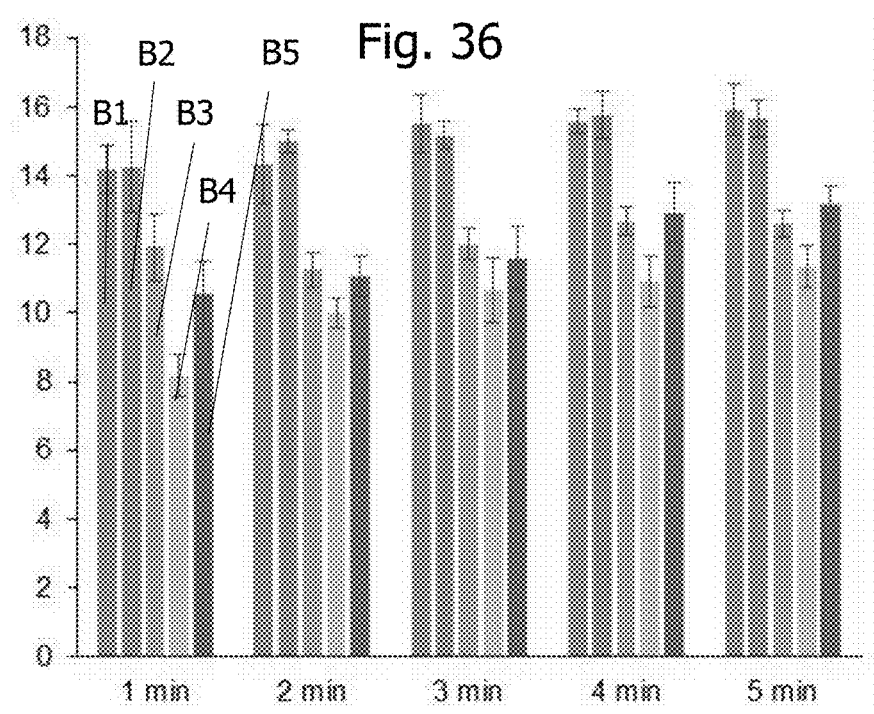
FIG. 36 a bar graph of the results of inhibition zone tests for all microorganisms for the EWC electrode of the second therapeutic device, FIG. 37 an illustration of the agar plates for an inhibition zone test for the third therapeutic device for the bacterium *Staphylococcus aureus,*

FIG. 36 shows a comparison of the diameter values for the bacteria *Staphylococcus aureus* (bar B1), *Staphylococcus epidermidis* (bar B2), *Escherichia coli* (bar B3), *Pseudomonas aeruginosa* (bar B4) and the yeast *Candida albicans* (bar B5). The treatment duration in minutes was plotted on the abscissa and the inhibition zone diameter in mm on the ordinate. The gram-positive bacteria *Staphylococcus aureus* (14.17-15.92 mm) and *Staphylococcus epidermidis* (14.25-15.67 mm) showed the largest inhibition zone diameters, while the gram-negative strains *Escherichia coli* (11.92-12.58 mm) and *Pseudomonas aeruginosa* (8.17-11.33 mm) and the yeast *Candida albicans* (10.54-13.17 mm) were less affected by plasma treatment with the EWC electrode.

For each series of tests, a decrease in antimicrobial efficacy was noted in the following order:

Staphylococcus epidermidis=Staphylococcus aureus>Escherichia coli≥Candida albicans>Pseudomonas aeruginosa.

The size of the growth inhibition zone increased with increasing treatment duration. In the period from 1 min to 5 min an increase of 5% for the bacterium *Escherichia coli* up to 28% for the bacterium *Pseudomonas aeruginosa* was observed.

As for the first therapeutic device (TV1), growth inhibition zone tests were performed for the third therapeutic device (TV3) for the same microorganisms.

Figure 37:
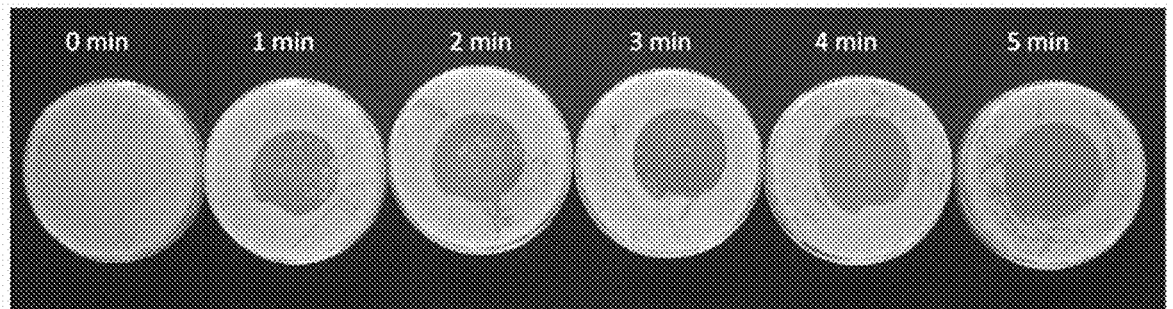

For the bacterium *Staphylococcus aureus*, they are shown in FIG. 37 at times t=0 min to t=5 min.

Figure 38:
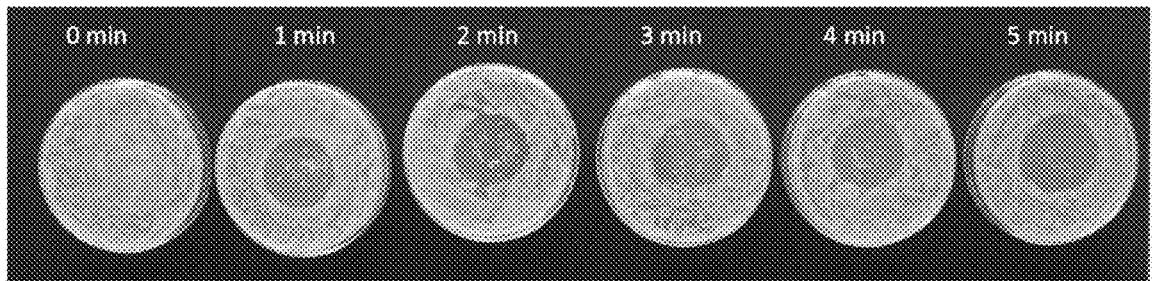
FIG. 38 an illustration of the agar plates for an inhibition zone test for the third therapeutic device for the bacterium *Staphylococcus epidermidis,*

For the bacterium *Staphylococcus epidermidis* they are shown in FIG. 38 at times t=0 min to t=5 min.

Figure 39:
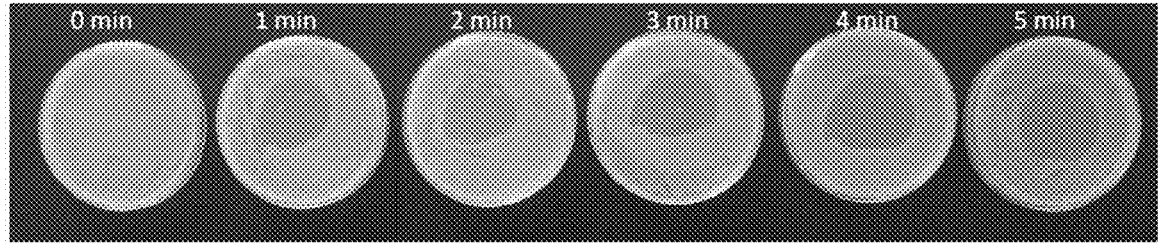
FIG. 39 an illustration of the agar plates for an inhibition zone test for the third therapeutic device for the bacterium *Escherichia coli,*

For the bacterium *Escherichia coli*, they are shown in FIG. 39 at times t=0 min to t=5 min.

Figure 40:
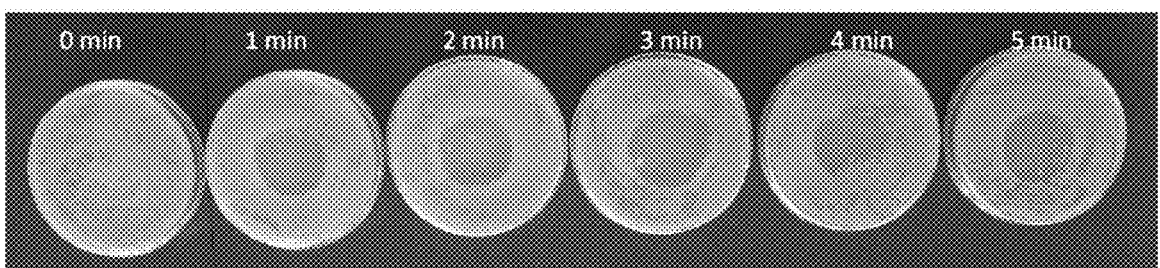
FIG. 40 an illustration of the agar plates for an inhibition zone test for the third therapeutic device for the bacterium *Pseudomonas aeruginosa,*

For the bacterium *Pseudomonas aeruginosa* they are shown in FIG. 40 at times t=0 min to t=5 min.

Figures 41, 42:
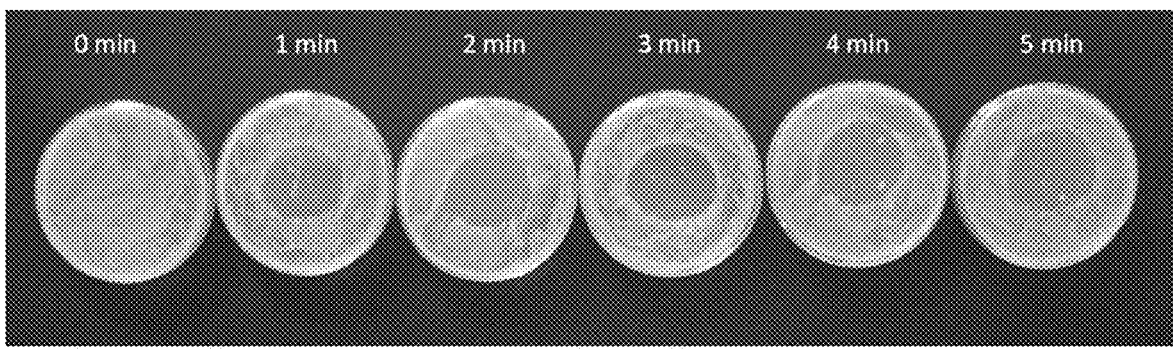
FIG. 41 an illustration of the agar plates for an inhibition zone test for the third therapeutic device for the yeast *Candida albicans,*
FIG. 42 a bar graph of the results of the inhibition zone tests for all microorganisms for the third therapeutic device.

For the yeast *Candida albicans* they are shown in FIG. 41 at times t=0 min to t=5 min.

FIG. 42 shows a comparison of the diameter values for the bacteria *Staphylococcus aureus* (bar B1), *Staphylococcus*

34

*epidermidis* (bar B2), *Escherichia coli* (bar B3), *Pseudomonas aeruginosa* (bar B4) and the yeast *Candida albicans* (bar B5). The treatment duration in minutes was plotted on the abscissa and the inhibition zone diameter in mm on the ordinate. The gram-positive bacterium *Staphylococcus aureus* (41.67-46.42 mm) showed the largest inhibition zone diameter. The second gram-positive bacterium *Staphylococcus epidermidis* (36.42-41.83 mm) as well as the gram-negative strains *Escherichia coli* (35.50-41.00 mm), *Pseudomonas aeruginosa* (35.00-38.75 mm) and the yeast *Candida albicans* (18.42-39.00 mm) were less affected by the plasma treatment. For the yeast *Candida albicans*, no growth inhibition zone could be determined for 5 Petri dishes at longer treatment times (t=3, 4, 5 min)

For each series of tests, a decrease in antimicrobial efficacy was noted in the following order:

Staphylococcus aureus>Staphylococcus epidermidis=Escherichia coli (≥Candida albicans for 1 and 2 min)>Pseudomonas aeruginosa.

The size of the inhibition zone increased in some cases with increasing treatment duration. The results for *Staphylococcus aureus* were comparable and therefore consistent.

Table 10 shows a comparison of the measurement results from the above measurement examples for the first, second and third therapeutic devices (TV1, TV2, TV3). Any officially specified limit values (L) are also included in the overview for orientation. The results for the patient leakage current (I), the temperature, the UV radiation and the concentrations of the emitted gases are within the safety limits.

TABLE 10

| Ex. Nr. | Parameter | Dim. | L | TV1 (HI) | TV2 (HI) | TV3 (HI) |
|---|---|---|---|---|---|---|
| 1 | I | μA | 100 | 12 | 11 | 16 |
| 2 | $E_{eff}$ | μW/cm² | — | 0.14 ± 0.2 | 0.16 | 0.86 ± 0.07 |
| 2 | $t_{max}$ | h, min | — | 6 h | 5 h | 1 h |
| 5 | ΔpH(5 min) | — | — | 2.43 | 2.43 | 2.86 |
| 5 | $H_2O_2$ (5 min) | μM | — | 44.35 | 81 ± 20 | 24.16 ± 9.3 |
| 5 | $NO_3^-$ (5 min) | μM | — | 49.4 ± 10.8 | 27.896 ± 4.36 | 24.8 ± 11.5 |
| 5 | $NO_2^-$ (5 min) | μM | — | 16.0 ± 3.9 | 11.67 ± 2.21 | 8.82 ± 2.1 |
| 6 | DM | IC-50 s | — | — | >300 | 65 |
| 7 | S. Aureus DM | mm | — | 17.2 | 15.92 | 44.80 |
| 7 | S. epidermidis DM | mm | — | 22.3 | 15.67 | 36.40 |
| 7 | E. Coli DM | mm | — | 15.0 | 12.58 | 35.90 |
| 7 | P. aeruginosa DM | mm | — | 12.6 | 11.33 | 38.80 |
| 7 | C. albicans DM | mm | — | 15.0 | 13.17 | 32.90 |
| 8 | IC-50 | s | — | >300 | 65 | >300 |

It is obvious to a person skilled in the art that many other variants are possible in addition to the embodiments described, without departing from the inventive concept. The subject of the invention is therefore not limited by the foregoing description and is to be determined by the scope of protection which is defined by the claims. For the interpretation of the claims or the description, the broadest possible reading of the claims is decisive. In particular, the terms "include" or "comprise" shall be construed as referring to elements, components, or steps in a non-exclusive sense, thereby indicating that the elements, components, or steps may be present or used that they can be combined with other elements, components or steps that are not explicitly mentioned. When the claims relate to an element or component from a group that may consist of A, B, C to N elements or components, this language should be interpreted as requiring only a single element of that group, and not a combination of A and N, B and N or any other combination of two or more elements or components of this group.

The invention claimed is:

1. A therapeutic device for cell stimulation or cell therapy, comprising a housing containing an electrode, a generator for generating high-frequency voltage pulses, a processor comprising a controller, a regulator and a calculator, further comprising a memory, at least one operating element and a controllable modulator for controlling the generator, wherein the modulator is configured to generate a voltage pulse sequence comprising a plurality of voltage pulses, wherein the modulator is configured to adjust a frequency and duration of the voltage pulses, wherein the electrode, the generator, the processor, the memory, the operating element and the modulator are arranged in the housing, wherein the electrode contains a glass body comprising a cavity containing a gas, wherein the electrode comprises a first end which is configured to be coupled to the modulator, wherein the electrode comprises a second dome-shaped end, wherein the gas is configured to be transformed into the state of a non-thermal primary plasma by the voltage pulses transmitted to the electrode, wherein a secondary plasma is configured to be generated by ionizing the air present in the region surrounding the second end of the electrode.

2. The therapeutic device of claim 1, wherein the frequency of the voltage pulse sequence is at least partially not constant.

3. The therapeutic device of claim 1, wherein the amplitude of the voltage increases during a period of time t2-t1 and is constant during a period of time t3-t2 and decreases during a period of time t4-t3, wherein the duration of the voltage pulse sequence corresponds to the period of time t4-t1.

4. The therapeutic device of claim 3, wherein the frequency increases during the period t2-t1, is constant during the period t3-t2 and decreases during the period t4-t3.

5. The therapeutic device of claim 1, wherein the maximum frequency is in the range of 10 up to and including 100 Hz.

6. The therapeutic device of claim 1, wherein the voltage at the output of the modulator is in the range of 8 V up to and including 65 V.

7. The therapeutic device of claim 1, wherein the voltage at the output of the generator is in the range of 5 kV up to and including 25 kV.

8. The therapeutic device of claim 1, wherein an energy storage arranged in the housing is provided for supplying energy for the operation of the therapeutic device, so that the therapeutic device is configured to be operated wirelessly.

9. The therapeutic device of claim 1, wherein the electrode comprises a sensor by means of which the current or the voltage emitted via the electrode is configured to be recorded as a measured value, wherein the measured value is configured to be digitized in measured data, wherein the measured data are configured to be stored in the memory, wherein the calculator of the processor is configured to determine at least one of an energy delivered or a time profile of the energy delivered by the electrode.

10. The therapeutic device of claim 9, wherein the controller of the processor is configured to control the modulator on the basis of the measured data.

11. The therapeutic device of claim 9, wherein the measured data are configured to control a course of therapy by means of the controller of the processor.

12. The therapeutic device of claim 11, wherein the measured data in the processor are configured to be linked to a time stamp, wherein the measured data linked to the time stamp are configured to be stored in the memory for storing the course of therapy.

13. The therapeutic device of claim 1, wherein the housing is configured as one of the poles of a capacitor for capacitive coupling.

14. The therapeutic device of claim 1, wherein the energy storage is configured as a rechargeable element.

15. The therapeutic device of claim 14, wherein the energy storage includes a negative pole configured as one of the poles of a capacitor for a capacitive coupling.

16. The therapeutic device of claim 1, wherein the housing comprises an inner side which contains one of an electrically conductive or conductable surface.

17. The therapeutic device of claim 16, wherein the electrically conductive or conductable surface comprises at least one of a conductive plastic or a plastic coated with an electrically conductable material.

18. The therapeutic device of claim 1, wherein the controller of the processor is configured to control the modulator for controlling the generator to generate one of a constant energy output or any desired signal form.

19. The therapeutic device of claim 18, wherein the desired signal form comprises one of an amplitude modulation or a frequency modulation.

* * * * *